(12) United States Patent
Khanna et al.

(10) Patent No.: US 7,256,011 B2
(45) Date of Patent: *Aug. 14, 2007

(54) ENZYME ACTIVATION PROTEASE ASSAY

(75) Inventors: Pyare Khanna, Fremont, CA (US);
Peter Fung, Sunnyvale, CA (US);
Joseph L. Horecka, Fremont, CA (US)

(73) Assignee: Discoverx Inc., Fremont, CA (US)

( * ) Notice: Subject to any disclaimer, the term of this patent is extended or adjusted under 35 U.S.C. 154(b) by 559 days.

This patent is subject to a terminal disclaimer.

(21) Appl. No.: 10/353,908

(22) Filed: Jan. 28, 2003

(65) Prior Publication Data

US 2003/0170770 A1  Sep. 11, 2003

Related U.S. Application Data

(60) Provisional application No. 60/352,780, filed on Jan. 29, 2002.

(51) Int. Cl.
*C12Q 1/37* (2006.01)
(52) U.S. Cl. ........................................................ 435/23
(58) Field of Classification Search .................. 435/23, 435/24, 14, 18, 4, 69.7, 69.8, 70.1, 975, 173.4, 435/207
See application file for complete search history.

(56) References Cited

U.S. PATENT DOCUMENTS 5,223,393 A * 6/1993 Khanna et al. ................ 435/6
5,434,052 A * 7/1995 Khanna ...................... 435/7.6
2004/0146956 A1* 7/2004 Khanna et al. ............ 435/7.92

OTHER PUBLICATIONS

Eglen, R. M., Assay &Drug Dev. Tech., vol. 1(1), pp. 97-104, (Nov. 2002)(Abstract Only).*
Webster's II New Riverside University Dictionary, p. 946 (1994).*
HitHunter Enzyme Fragment Complementation, Cyclic-AMP Assay Kit DaTA Sheet, (Copyright 2001).*
Eglen, 2002.ASSAY and Drug Development Technologies, vol. 1, No. 1, pp. 97-104.*

* cited by examiner

*Primary Examiner*—Jon Weber
*Assistant Examiner*—Kailash C. Srivastava
(74) *Attorney, Agent, or Firm*—David J. Aston; Bertram I. Rowland; Peters Verny, LLP

(57) ABSTRACT

A protein reagent is provided for measuring protease enzyme activity in a sample. The protein reagent comprises two inhibition entities joined by a linker comprised of an indicator enzyme donor and an amino acid sequence susceptible to enzymatic cleavage. The protein reagent is substantially inhibited from binding to the cognate enzyme acceptor fragment, while the product of the enzymatic cleavage binds to the cognate enzyme acceptor fragment to form a functional indicator enzyme. The indicator enzyme activity is related to the protease enzyme activity of the sample.

20 Claims, 14 Drawing Sheets

Figure 1A

CTCGAGAAATCATAAAAAATTTATTTGCTTTGTGAGCGGATAACAATTATAATAGAT
TCAATTGTGAGCGGATAACAATTTCACACAGAATTCATTAAAGAGGAGAAATTAAC
TATGAGAGGATCGCATCACCATCACCATCACGGATCCAGCTCCAATTCACTGGCCGT
CGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCC
CTTCCCAACAGTTGCGCAGCCTGAATGGCGAAGCATGCGAGCTCGGTACCAGATCT
GTCGACcacaagtgcgatatcaccttacaggagatcatcaaaactttgaacagcctcacagagcagaagactctgtgcaccgagttga
ccgtaacagacatctttgctgcctccaagaacacaactgagaaggaaaccttctgcagggctgcgactgtgctccggcagttctacagcca
ccatgagaaggacactcgctgcctgggtgcgactgcacagcagttccacaggcacaagcagctgatccgattcctgaaacggctcgaca
ggaacctctggggcctggcgggcttgaattcctgtcctgtgaaggaagccaaccagagtacgttggaaaacttcttggaaaggctaaagac
gatcatgagagagaaatattcaaagtgttcgagctgaAAGCTTAATTAGCTGAGCTTGGACTCCTGTTGAT
AGATCCAGTAATGACCTCAGAACTCCATCTGGATTTGTTCAGAACGCTCGGTTGCCG
CCGGGCGTTTTTTATTGGTGAGAATCCAAGCTAGCTTGGCGAGATTTTCAGGAG
CTAAGGAAGCTAAAATGGAGAAAAAAATCACTGGATATACCACCGTTGATATATCC
CAATGGCATCGTAAAGAACATTTTGAGGCATTTCAGTCAGTTGCTCAATGTACCTAT
AACCAGACCGTTCAGCTGGATATTACGGCCTTTTTAAAGACCGTAAAGAAAAATAA
GCACAAGTTTTATCCGGCCTTTATTCACATTCTTGCCCGCCTGATGAATGCTCATCCG
GAATTTCGTATGGCAATGAAAGACGGTGAGCTGGTGATATGGGATAGTGTTCACCCT
TGTTACACCGTTTTCCATGAGCAAACTGAAACGTTTTCATCGCTCTGGAGTGAATAC
CACGACGATTTCCGGCAGTTTCTACACATATATTCGCAAGATGTGGCGTGTTACGGT
GAAAACCTGGCCTATTTCCCTAAAGGGTTTATTGAGAATATGTTTTCGTCTCAGCCA
ATCCCTGGGTGAGTTTCACCAGTTTTGATTTAAACGTGGCCAATATGGACAACTTCTT
CGCCCCCGTTTTCACCATGGGCAAATATTATACGCAAGGCGACAAGGTGCTGATGCC
GCTGGCGATTCAGGTTCATCATGCCGTTTGTGATGGCTTCCATGTCGGCAGAATGCT
TAATGAATTACAACAGTACTGCGATGAGTGGCAGGGCGGGGCGTAATTTTTTAAGG
CAGTTATTGGTGCCCTTAAACGCCTGGGGTAATGACTCTCTAGCTTGAGGCATCAAA
TAAAACGAAAGGCTCAGTCGAAAGACTGGGCCTTTCGTTTTATCTGTTGTTTGTCGG
TGAACGCTCTCCTGAGTAGGACAAATCCGCCCTCTAGAGCTGCCTCGCGCGTTTCGG
TGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCG
GGTGTCGGGGCGCAGCCATGACCCAGTCACGTAGCGATAGCGGAGTGTATACTGGC
TTAACTATGCGGCATCAGAGCAGATTGTACTGAGAGTGCACCATATGCGGTGTGAA
ATACCGCACAGATGCGTAAGGAGAAAATACCGCATCAGGCGCTCTTCCGCTTCCTCG
CTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAG
AGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCG

Figure 1B

```
CCACTGGCAGCAGCCACTGGTAACAGGATTAGCAGAGCGAGGTATGTAGGCGGTGC
TACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGATC
CGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGA
TCTTCACCTAGATCCTTTTAAATTAAAAATGAAGTTTTAAATCAATCTAAAGTATATA
TGAGTAAACTTGGTCTGACAGTTACCAATGCTTAATCAGTGAGGCACCTATCTCAGC
GATCTGTCTATTTCGTTCATCCATAGTTGCCTGACTCCCCGTCGTGTAGATAACTACG
ATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGC
CCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACC
AGCGTTTCTGGGTGAGCAAAAACAGGAAGGCAAAATGC
CGCAAAAAAGGGAATAAGGGCGACACGGAAATGTTGAATACTCATACTCTTCCTTTT
TCAATATTATTGAAGCATTTATCAGGGTTATTGTCTCATGAGCGGATACATATTTGA
ATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTA
TCACGAGGCCCTTTCGTCTTCAC
```

(SEQ ID: NO. 1)

Lanes: 1 = MC1061 cells (-IPTG)
2 = MC1061 cells (+IPTG)
3 = pGEX6P-1 ctrl cells (-IPTG)
4 = pGEX6P-1 ctrl cells (+IPTG)
5 = pGEX6P-1 +ED-IL4 #2 (-IPTG)
6 = pGEX6P-1 +ED-IL4 #2 (+IPTG)
7 = pGEX6P-1 +ED-IL4 #40 (-IPTG)
8 = pGEX6P-1 +ED-IL4 #40 (+IPTG)
9 = pGEX6P-1 +ED-IL4 #5 {Negative control} (-IPTG)
10 = pGEX6P-1 +ED-IL4 #5 {Negative control} (+IPTG)

Lanes:
1 = pGEX6P-1 ctrl cells (-IPTG)
2 = pGEX6P-1 ctrl cells (+IPTG)
3 = pGEX6P-1 +ED-IL4 #2 (-IPTG)
4 = pGEX6P-1 +ED-IL4 #2 (+IPTG)
5 = pGEX6P-1 +ED-IL4 #40A (-IPTG)
6 = pGEX6P-1 +ED-IL4 40A (+IPTG)
7 = pGEX6P-1 +ED-IL4 #40B (-IPTG)
8 = pGEX6P-1 +ED-IL4 #40B (+IPTG)

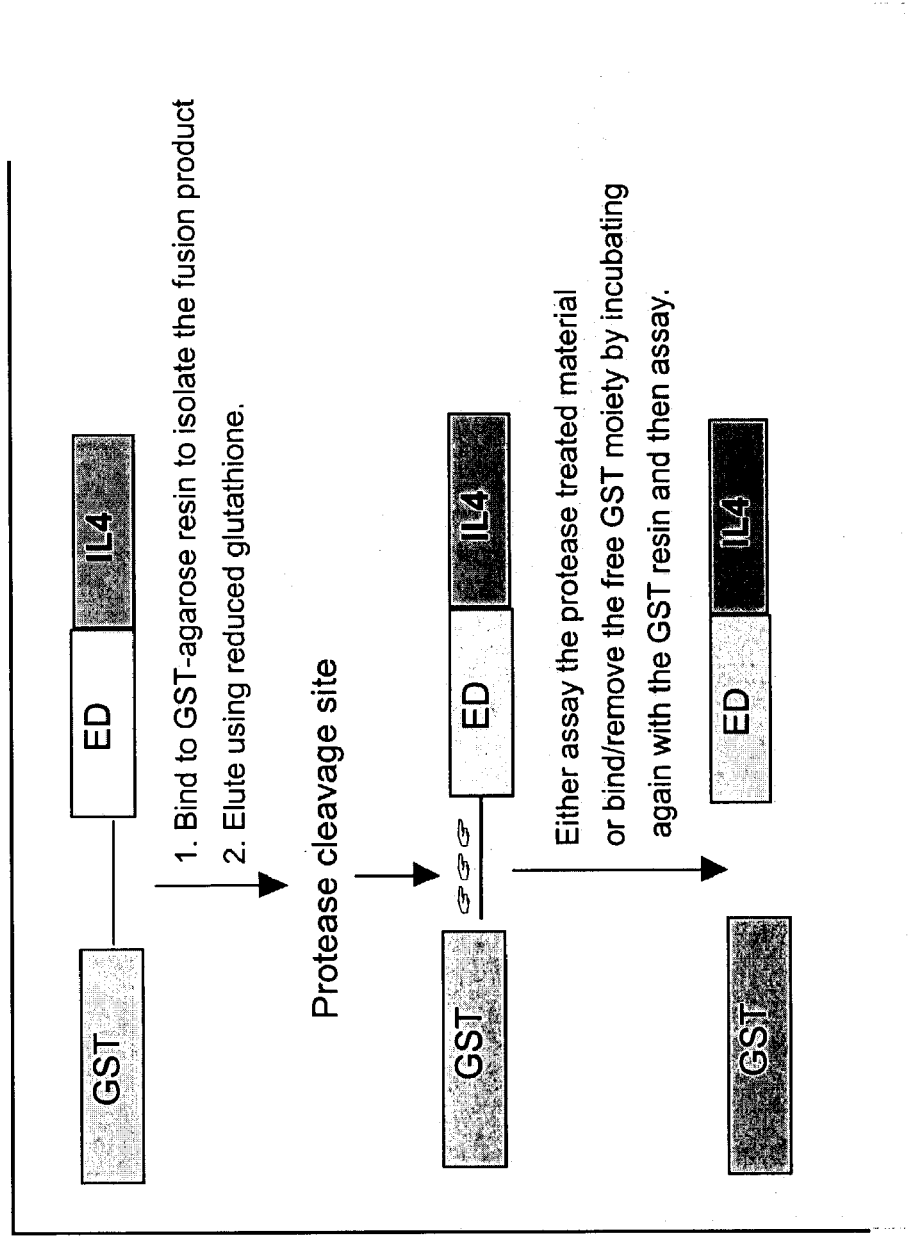

Figure 8A

```
   1 tagttattaa tagtaatcaa ttacggggtc attagttcat agcccatata tggagttccg
  61 cgttacataa cttacggtaa atggcccgcc tggctgaccg cccaacgacc cccgcccatt
 121 gacgtcaata atgacgtatg ttcccatagt aacgccaata gggactttcc attgacgtca
 181 atgggtggag tatttacggt aaactgccca cttggcagta catcaagtgt atcatatgcc
 241 aagtacgccc cctattgacg tcaatgacgg taaatggccc gcctggcatt atgcccagta
 301 catgacctta tgggactttc ctacttggca gtacatctac gtattagtca tcgctattac
 361 catggtgatg cggttttggc agtacatcaa tgggcgtgga tagcggtttg actcacgggg
 421 atttccaagt ctccacccca ttgacgtcaa tgggagtttg ttttggcacc aaaatcaacg
 481 ggactttcca aaatgtcgta acaactccgc cccattgacg caaatgggcg gtaggcgtgt
 541 acggtgggag gtctatataa gcagagctgg tttagtgaac cgtcagatcc gctagcgcta
 601 ccggtatgtc ccctatacta ggttattgga aaattaaggg ccttgtgcaa cccactcgac
 661 ttcttttgga atatcttgaa gaaaaatatg aagagcattt gtatgagcgc gatgaaggtg
 721 ataaatggcg aaacaaaaag tttgaattgg gtttggagtt tcccaatctt ccttattata
 781 ttgatggtga tgttaaatta acacagtcta tggccatcat acgttatata gctgacaagc
 841 acaacatgtt gggtggttgt ccaaaagagc gtgcagagat tcaatgctt gaaggagcgg
 901 ttttggatat tagatacggt gtttcgagaa ttgcatatag taaagacttt gaaactctca
 961 aagttgattt tcttagcaag ctacctgaaa tgctgaaaat gttcgaagat cgtttatgtc
1021 ataaaacata tttaaatggt gatcatgtaa cccatcctga cttcatgttg tatgacgctc
1081 ttgatgttgt tttatacatg gacccaatgt gcctggatgc gttcccaaaa ttagtttgtt
1141 ttaaaaaacg tattgaagct atcccacaaa ttgataagta cttgaaatcc agcaagtata
1201 tagcatggcc tttgcagggc tggcaagcca cgtttggtgg tggcgaccat cctccaaaat
1261 cggataaacc ggtcgccacc atgagctcca attcactggc cgtcgtttta caacgtcgtg
1321 actgggaaaa ccctggcgtt acccaactta atcgccttgc agcacatccc cctttcgcca
1381 gctggcgtaa tagcgaagag gcccgcaccg atcgccctc ccaacagttg cgcagcctga
1441 atggcgaacc ggactcagat ctcgagatcg aaggtcgtat ggggcaaccc gggaacggca
1501 gcgccttctt gctggcaccc aatagaagcc atgcgccgga ccacgacgtc acgcagcaaa
1561 gggacgaggt gtgggtggtg ggcatgggca tcgtcatgtc tctcatcgtc ctggccatcg
1621 tgtttggcaa tgtgctggtc atcacagcca ttgccaagtt cgagcgtctg cagacggtca
1681 ccaactactt catcacttca ctggcctgtg ctgatctggt catgggcctg gcagtggtgc
1741 cctttggggc cgcccatatt cttatgaaaa tgtggacttt tggcaacttc tggtgcgagt
1801 tttggacttc cattgatgtg ctgtgcgtca cggccagcat tgagaccctg tgcgtgatcg
1861 cagtggatcg ctactttgcc attacttcac ctttcaagta ccagagcctg ctgaccaaga
1921 ataaggcccg ggtgatcatt ctgatggtgt ggattgtgtc aggccttacc tccttcttgc
1981 ccattcagat gcactggtac cgggccaccc accaggaagc catcaactgc tatgccaatg
2041 agacctgctg tgacttcttc acgaaccaag cctatgccat tgcctcttcc atcgtgtcct
2101 tctacgttcc cctggtgatc atggtcttcg tctactccag ggtctttcag gaggccaaaa
2161 ggcagctcca gaagattgac aaatctgagg gccgcttcca tgtccagaac cttagccagg
2221 tggagcagga tgggcggacg gggcatggac tccgcagatc ttccaagttc tgcttgaagg
2281 agcacaaagc cctcaagacg ttaggcatca tcatgggcac tttcaccctc tgctggctgc
2341 ccttcttcat cgttaacatt gtgcatgtga tccaggataa cctcatccgt aaggaagttt
2401 acatcctcct aaattggata ggctatgtca attctggttt caatcccctt atctactgcc
```

Figure 8B 2461 ggagcccaga tttcaggatt gccttccagg agcttctgtg cctgcgcagg tcttctttga
2521 aggcctatgg gaatggctac tccagcaacg gcaacacagg ggagcagagt ggatatcacg
2581 tggaacagga gaaagaaaat aaactgctgt gtgaagacct cccaggcacg gaagactttg
2641 tgggccatca aggtactgtg cctagcgata acattgattc acaagggagg aattgtagta
2701 caaatgactc actgctgtaa ggatccaccg gatctagata actgatcata atcagccata
2761 ccacatttgt agaggtttta cttgctttaa aaaacctccc acacctcccc ctgaacctga
2821 aacataaaat gaatgcaatt gttgttgtta acttgtttat tgcagcttat aatggttaca
2881 aataaagcaa tagcatcaca aattcacaa ataaagcatt tttttcactg cattctagtt
2941 gtggtttgtc caaactcatc aatgtatctt aacgcgtaaa ttgtaagcgt taatatttg
3001 ttaaaattcg cgttaaattt ttgttaaatc agctcatttt ttaaccaata ggccgaaatc
3061 ggcaaaatcc cttataaatc aaaagaatag accgagatag ggttgagtgt tgttccagtt
3121 tggaacaaga gtccactatt aaagaacgtg gactccaacg tcaaagggcg aaaaaccgtc
3181 tatcagggcg atggcccact acgtgaacca tcacctaat caagttttt ggggtcgagg
3241 tgccgtaaag cactaaatcg gaaccctaaa gggagccccc gatttagagc ttgacgggga
3301 aagccggcga acgtggcgag aaaggaaggg aagaaagcga aaggagcggg cgctagggcg
3361 ctggcaagtg tagcggtcac gctgcgcgta accaccacac ccgccgcgct taatgcgccg
3421 ctacagggcg cgtcaggtgg cacttttcgg ggaaatgtgc gcggaacccc tatttgttta
3481 tttttctaaa tacattcaaa tatgtatccg ctcatgagac aataaccctg ataaatgctt
3541 caataatatt gaaaaaggaa gagtcctgag gcggaaagaa ccagctgtgg aatgtgtgtc
3601 agttagggtg tggaaagtcc ccaggctccc cagcaggcag aagtatgcaa agcatgcatc
3661 tcaattagtc agcaaccagg tgtggaaagt ccccaggctc cccagcaggc agaagtatgc
3721 aaagcatgca tctcaattag tcagcaacca gtagtcccgcc cctaactccg cccatcccgc
3781 ccctaactcc gcccagttcc gcccattctc cgccccatgg ctgactaatt ttttttattt
3841 atgcagaggc cgaggccgcc tcggcctctg agctattcca gaagtagtga ggaggcttt
3901 ttggaggcct aggcttttgc aaagatcgat caagagacag gatgaggatc gtttcgcatg
3961 attgaacaag atggattgca cgcaggttct ccggccgctt gggtggagag gctattcggc
4021 tatgactggg cacaacagac aatcggctgc tctgatgccg ccgtgttccg gctgtcagcg
4081 caggggcgcc cggttctttt tgtcaagacc gacctgtccg gtgccctgaa tgaactgcaa
4141 gacgaggcag cgcggctatc gtggctggcc acgacgggcg ttccttgcgc agctgtgctc
4201 gacgttgtca ctgaagcggg aagggactgg ctgctattgg gcgaagtgcc ggggcaggat
4261 ctcctgtcat ctcaccttgc tcctgccgag aaagtatcca tcatggctga tgcaatgcgg
4321 cggctgcata cgcttgatcc ggctacctgc ccattcgacc accaagcgaa acatcgcatc
4381 gagcgagcac gtactcggat ggaagccggt cttgtcgatc aggatgatct ggacgaagag
4441 catcaggggc tcgcgccagc cgaactgttc gccaggctca aggcgagcat gcccgacggc
4501 gaggatctcg tcgtgaccca tggcgatgcc tgcttgccga atatcatggt ggaaaatggc
4561 cgcttttctg gattcatcga ctgtggccgg ctgggtgtgg cggaccgcta tcaggacata
4621 gcgttggcta cccgtgatat tgctgaagag cttggcggcg aatgggctga ccgcttcctc
4681 gtgctttacg gtatcgccgc tcccgattcg cagcgcatcg ccttctatcg ccttcttgac
4741 gagttcttct gagcgggact ctggggttcg aaatgaccga ccaagcgacg cccaacctgc
4801 catcacgaga tttcgattcc accgccgcct tctatgaaag gttgggcttc ggaatcgttt
4861 tccgggacgc cggctggatg atcctccagc gcggggatct catgctggag ttcttcgccc

Figure 8C 4921 accctagggg gaggctaact gaaacacgga aggagacaat accggaagga acccgcgcta
4981 tgacggcaat aaaaagacag aataaaacgc acggtgttgg gtcgtttgtt cataaacgcg
5041 gggttcggtc ccagggctgg cactctgtcg atacccacc gagaccccat tggggccaat
5101 acgcccgcgt ttcttccttt tccccacccc accccccaag ttcgggtgaa ggcccagggc
5161 tcgcagccaa cgtcggggcg gcaggccctg ccatagcctc aggttactca tatatacttt
5221 agattgattt aaaacttcat ttttaattta aaaggatcta ggtgaagatc cttttttgata
5281 atctcatgac caaaatccct taacgtgagt tttcgttcca ctgagcgtca gaccccgtag
5341 aaaagatcaa aggatcttct tgagatcctt ttttttctgcg cgtaatctgc tgcttgcaaa
5401 caaaaaaacc accgctacca gcggtggttt gtttgccgga tcaagagcta ccaactcttt
5461 ttccgaaggt aactggcttc agcagagcgc agataccaaa tactgtcctt ctagtgtagc
5521 cgtagttagg ccaccacttc aagaactctg tagcaccgcc tacatacctc gctctgctaa
5581 tcctgttacc agtggctgct gccagtggcg ataagtcgtg tcttaccggg ttggactcaa
5641 gacgatagtt accggataag gcgcagcggt cgggctgaac ggggggttcg tgcacacagc
5701 ccagcttgga gcgaacgacc tacaccgaac tgagatacct acagcgtgag ctatgagaaa
5761 gcgccacgct tcccgaaggg agaaaggcgg acaggtatcc ggtaagcggcagggtcggaa
5821 caggagagcg cacgagggag cttccagggg gaaacgcctg gtatctttat agtcctgtcg
5881 ggtttcgcca cctctgactt gagcgtcgat ttttgtgatg ctcgtcaggg gggcggagcc
5941 tatggaaaaa cgccagcaac gcggccttttt tacggttcct ggccttttgc tggccttttg
6001 ctcacatgtt ctttcctgcg ttatcccctg attctgtgga taaccgtatt accgccatgc
6061 at (SEQ ID: NO. 6)

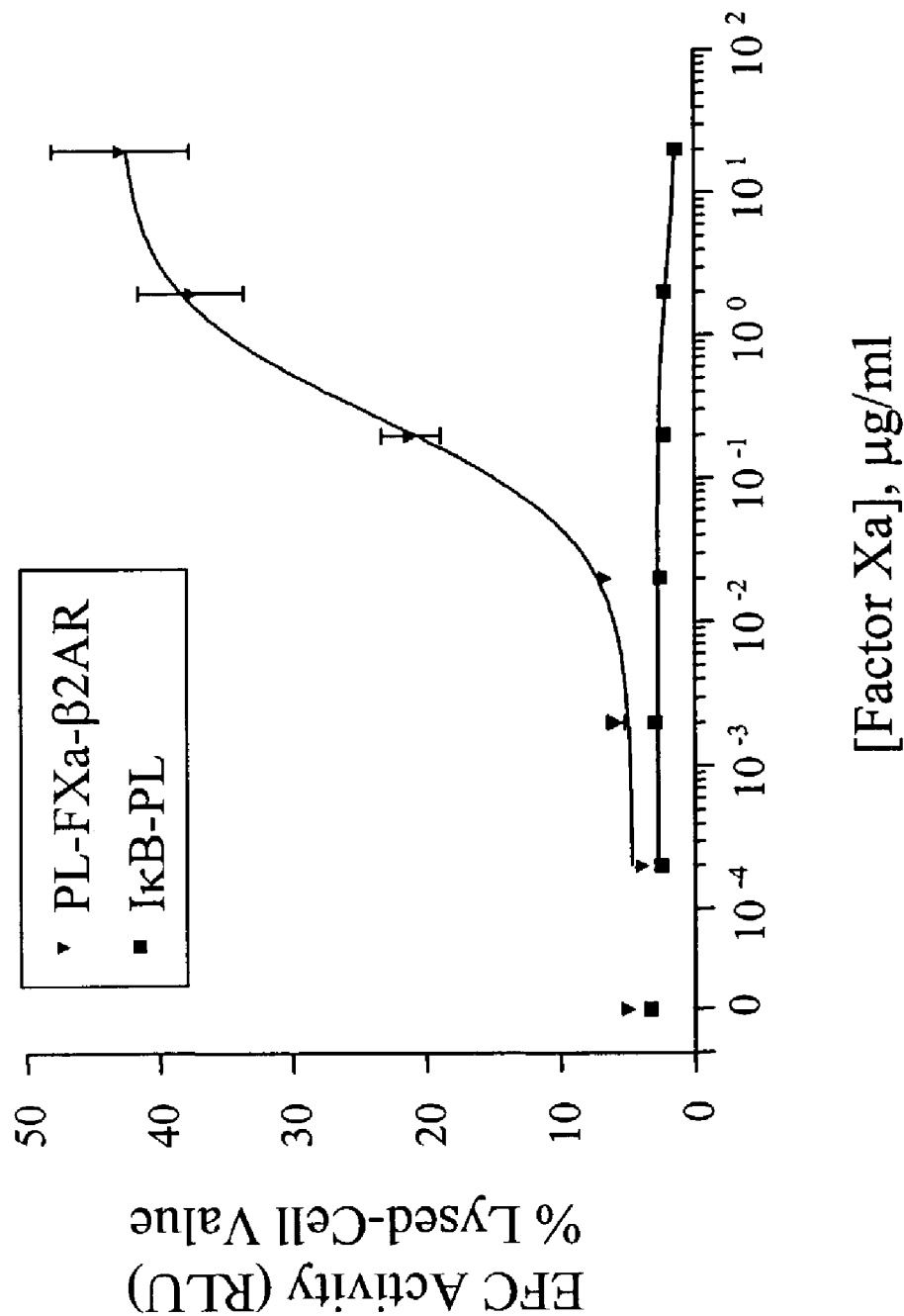

ENZYME ACTIVATION PROTEASE ASSAY

REFERENCE TO PRIOR APPLICATIONS

This application claims priority to U.S. Provisional Application serial no. 60/352,780, filed 29 Jan. 2002.

BACKGROUND OF THE INVENTION

1. Field of the Invention

The invention is in the field of protease assays.

2. Background Information

Proteases play a vital role in the viability and regulation of cellular activity. Proteases act by inter- and intramolecular mechanisms, to activate and inactivate proteins, and regulate expression of proteins by their action with transcription factors and transcription factor regulating proteins. Proteases are active in blood clotting and embolism dissolution, apoptosis, inflammatory activity, processing of proteins, metabolism, degradation of proteins, etc. The processes are greatly varied as to their action, mechanism and function. Proteases come within the class of hydrolases, hydrolyzing amide bonds. For this purpose, there are numerous classes of proteins, such as the serine/threonine hydrolases, metalloproteinases, cysteine proteases, etc. While many proteases are promiscuous in their recognition sequences, such as trypsin, chymotrypsin, bromelain, papain, etc., having fairly common recognition sites, many other proteases have recognition sequences that are rare except for the particular protease substrate. In addition, there are many microorganisms that depend upon specific protease activity for their infectivity. Being able to inhibit proteases essential to the viability of the organism would diminish its infectivity. Viruses depend, to a great degree, on express proproteins that are cleaved to active products. Inhibiting such selective cleavage would inhibit the viability of the virus. There is, therefore, an interest in providing methods that can detect the presence of a specific protease in a sample, be capable of being used for rapid screening, be sensitive to the particular protease at low concentrations of the protease, while being reasonably stable to other proteases, and provide for a ready reliable readout.

Recently, in WO 00/39348 and references cited therein, a system is described that employs α-complementation between a small fragment of β-galactosidase called the enzyme donor fragment ("ED") and a larger fragment referred to as the enzyme acceptor ("EA"), where the two fragments complex to form an active β-galactosidase. The method described in the aforementioned application fuses the ED to a protein of interest, where there is a recognition sequence in the protein of interest. The fusion protein is reported to have substantially less activity than the protease catalyzed product. This method has numerous deficiencies. One of the advantages of the ED use is that it is readily degraded intracellularly, so that ED, by itself, does not provide a background. Where the ED is cleaved from the protein of interest, it may be rapidly degraded, so as to confuse the result. Furthermore, the inhibition of complexing of ED to EA is difficulty achieved, so that the fusion protein will have significant activity. Since initially the fusion protein will be present in much greater amount than the cleavage product, one will be dealing with small differences in observed signal, substantially reducing the sensitivity of the assay.

RELEVANT LITERATURE

WO 00/039348, as indicated above, describes a protease assay where the marker is a β-galactosidase fragment fused to a protein having a specific protease cleavage site. There are numerous other references concerned with the use of β-galactosidase fragments in assay systems. The following are illustrative. Douglas, et al., Proc. Natl. Acad. Sci. USA 1984, 81:3983-7 describes the fusion protein of ATP-2 and lacZ. WO92/03559 describes a fusion protein employing α-complementation of β-galactosidase for measuring proteinases. WO01/0214 describes protein folding and/or solubility assessed by structural complementation using the α-peptide of β-galactosidase as a fusion protein. WO01/60840 describes fusion proteins including a fusion protein comprising an enzyme donor β-galactosidase for measuring protein folding and solubility. Homma, et al., Biochem. Biophys. Res. Commun., 1995, 215, 452-8 describes the effect of α-fragments of β-galactosidase on the stability of fusion proteins. Abbas-Terki, et al., Eur. J. Biochem. 1999, 266, 517-23 describes α-complemented β-galactosidase as an in vivo model substrate for the molecular chaperone heat-shock protein in yeast. Miller, et al., Gene, 1984, 29, 247-50 describes a quantitative β-galactosidase α-complementation assay for fusion proteins containing human insulin β-chain peptides. Thomas and Kunkel, Proc. Natl. Acad. Sci. USA, 1993, 90, 7744-8 describe an ED containing plasmid to measure mutation rate. WO98/42854 discloses non-independently complexing β-galactosidase fragments forming an active enzyme upon complexing of fused auxiliary proteins.

SUMMARY OF THE INVENTION

Target protease assays are provided comprising a protein reagent comprising first and second moieties linked by an enzyme donor fragment ("ED") and proximal to the ED is a protease recognition site, with the proviso that when one of the moieties is a surface, optionally only the surface hindering moiety need be present for hindrance. The protein reagent has low affinity for the enzyme acceptor fragment to form an active enzyme, while the proteolytic cleavage product has substantially enhanced activity and the cleavage product comprising the ED retains substantial stability in a cytosolic medium. By bringing together the protein reagent and a sample suspected of or comprising the protease(s) of interest, in the presence of the enzyme acceptor and enzyme substrate, the turnover rate of the substrate indicates the amount of protein reagent cleaved. The subject assays can be used to identify organisms or tissues, to screen for candidate compounds that serve as protease agonists or antagonists, and as bioassays for biological samples.

BRIEF DESCRIPTION OF THE FIGURES

FIG. 1 is a nucleotide sequence (SEQ ID NO: 1) of the fragment 600 bp HI/Bam HI fragment to ED-IL4;

FIG. 3 shows expression of the fusion protein product after induction with 0.1 mM IPTG displayed by Coomasie blue staining.

FIG. 4 shows schematic representation of the protocol followed to purify the inactive fusion construct and the cleaning and removing of the GST moiety away from the active ED-IL4 product;

FIG. 8 shows plasmid sequence (Seq. ID: No. 6);

FIG. 9 is a plot of the effect of FXa on lysis of cells; and

DETAILED DESCRIPTION OF THE INVENTION

Figure 2:
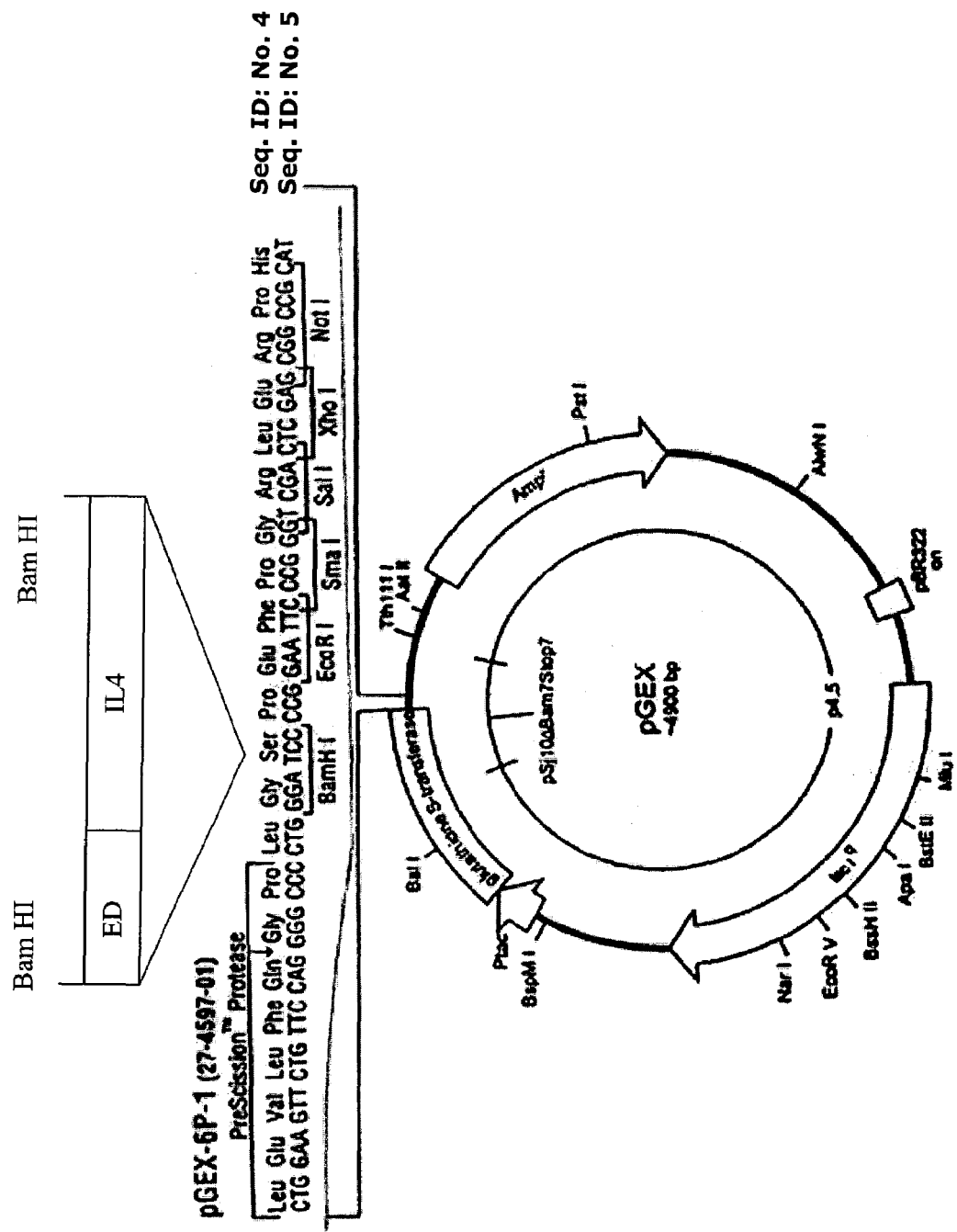
FIG. 2 shows the Bam HI ED-IL4 fragment ligated into pGEX 6p-1 plasmid to generate translated sequence (Seq. ID: No. 4) and DNA sequence (Seq. ID: No. 5)

Target protease assays are provided using a protein reagent that is specifically designed to be responsive to cleavage by one or a related family of target proteases and, upon cleavage, provide an entity that can be readily detected. The protein reagent comprises a fragment of an indicator enzyme referred to as the enzyme donor ("ED"), where the fragment may be derived from the N- or C-proximal portion of the indicator enzyme and will generally be an oligopeptide of less than 100 kDa. The ED will link two hindering entities, usually sterically hindering, wherein the linkage to at least one of the hindering entities comprises a protease recognition site, with the provison that when one of the hindering entities is a surface, only the surface hindering entity need be present to provide hindrance. Preferably, there will be two hindering entities. By hindering is intended that there is at least a 5-fold reduction in the activity of the ED in the presence of the EA when bound to the hindering entities. The protein reagent is substantially inhibited from binding to a complementary fragment of the cognate enzyme, referred to as the enzyme acceptor ("EA"), where the complex of the ED and EA results in a functional indicator enzyme.

The indicator enzymes and their fragments are required to have a number of characteristics. The fragments should be substantially inactive, in that there should be little, if any, background with only one fragment present in the presence of substrate. Secondly, the fragments should have sufficient affinity for each other, so that upon scission of one of the hindering entities from a fragment of the protein reagent, the fragments will combine to provide an active enzyme. The ED fragment of the protein reagent will complex with the EA fragment as a result of the affinity of the fragments of the enzyme for each other or as a result of being fused to auxiliary binding entities that will bring the enzyme fragments together resulting in an active enzyme. That is, in the former case, the enzyme fragments are capable of complexing without having an auxiliary binding entity to bring the fragments together to form a complex. In the latter case, the enzyme fragments will not independently form a complex, but when the auxiliary proteins form a complex, the enzyme fragments are then able to form an active enzyme.

Various indicator enzymes are known that fulfill these criteria and additional enzymes may be developed in accordance with known technologies. Indicator enzymes that fit these criteria include β-galactosidase (see U.S. Pat. No. 4,708,929), ribonuclease A (see U.S. Pat. No. 4,378,428), where the smaller fragment may come from the amino or carboxy terminus, β-lactamase (see WO 00/71702 AND 01/94617 and Wehrman, et al., Proc. Natl. Acad. Sci. 2002, 99, 3469-74), or enzymes that have small peptide cofactors, such as adenovirus proteases (see U.S. Pat. No. 5,935,840). To identify other indicator enzymes that can serve in place of the above indicator enzymes, enzyme genes may be cleaved asymmetrically to define a small and a large fragment, and expressed in the same and different cells. In the presence of the substrate, the cells producing both fragments would catalyze the reaction of the substrate, while there should be little, if any, turnover with the individual fragments. Alternatively, one may express the fragments individually and, if there is no reaction, combine the mixtures to see whether an enzyme-catalyzed reaction occurs. As for the enzyme fragments comprising auxiliary fragments, a number of enzymes are known whose fragments will complex to form an active enzyme, such as DHFR, and others may be determined as described above.

Indicator enzymes of interest are those that are below about 300 kDa, generally below about 150 kDa. The independently complexing small fragment will be under 15 kDa, more usually under about 10 kDa, frequently under about 125 amino acids, generally under about 100 amino acids and preferably not more than about 75 amino acids. Depending on the enzyme, the independently complexing ED may be as small as 10 amino acids, usually being at least about 25, more usually at least about 35 amino acids. With this criterion in mind, the fragments that are screened can be selected to provide the appropriately-sized small fragment.

The enzymes having fragments that complex in conjunction with a fused auxiliary protein will generally have fragments having from 20-80, more usually 25-75% of the amino acids of the enzyme. The fragments may be modified by the addition of from about 1 to 20, usually 2 to 10, amino acids to enhance the affinity of the fragments during complexation. Enzymes that provide for low affinity complexation to an active enzyme include β-galactosidase, β-glucuronidase, Staphylococcal nuclease, β-lactamase, as exemplary. The binding proteins may have as few as 8, more usually at least 10 amino acids and may be 150, usually not more than about 100 kDa. Binding proteins may include homo- and heterodimers, epitopes and immunoglobulins or fragments thereof, e.g., Fab, ligands and receptors, etc. In some instances, complexation may require the addition of an additional reagent, so that complexation with formation of an active enzyme does not occur to any significant degree in the absence of the additional reagent, e.g., FK1012, rapamycin and cyclosporin.

Each of the indicator enzymes will have an appropriate substrate. β-galactosidase uses effectively fluorescers having phenolic groups that are etherified with a β-galactosyl group. Ribonuclease A, fluorescer modified nucleotides, exemplified by 5'-O-acetyl 2'-O-(tetrahhydropyran-2-yl)uridine 3'-(4-methylumbelliferon-7-yl) ammonium phosphate, adenovirus proteinase, -(L, I, M)-X-G-G/X- or -(L, I, M)-X-G-X/G-, where the vertical line denotes the position of cleavage; the P3 (X) position appears to be unimportant for cleavage (Anderson, C. W., Virology, 177;259 (1990); Webster, et al., J. Gen. Virol., 70;3225 (1989)) and the peptide substrate can be designed to provide a detectable signal, e.g. using fluorescence resonance energy transfer, by having a fluorescer and a quencher on opposite sides of the cleavage site. β-Glucuronidase substrates are exemplified by 5-Br-4-Cl-3-indolyl β-D-glucuronidase.

Since β-galactosidase is paradigmatic of the peptides used in the subject invention, demonstrating the criteria for having two peptides that when combined complex non-covalently to form an active enzyme, this enzyme will be frequently referred to hereafter as illustrative of the class, except for those situations where the different enzymes must be considered independently. The ED for β-galactosidase is extensively described in the patent literature. U.S. Pat. Nos. 4,378,428; 4,708,929; 5,037,735; 5,106,950; 5,362,625; 5,464,747; 5,604,091; 5,643,734; and PCT application Nos. WO96/19732 and WO98/06648 describe assays using complementation of enzyme fragments. The β-galactosidase ED will generally be of at least about 35 amino acids, usually at least about 37 amino acids, frequently at least about 40 amino acids, and usually not exceed 100 amino acids, more usually not exceed 75 amino acids. The upper limit is defined by the effect of the size of the ED on the performance and purpose of the determination, the inconvenience of a larger construct, and the like. While the subject methodology has particular application for target proteases, the method may be used for any enzyme that results in the cleavage of a covalent bond, e.g., hydrolases, so as to make the ED accessible to the EA. By providing for ester linkages, either organic or inorganic, phosphate anhydrides, etc., for example, cleavage of such linkages would make the ED accessible. However, these protein reagents could not be directly synthesized by recombinant techniques and to that extent these types of assays are less attractive commercially.

The protein reagent may have the recognition sequence proximal to the N- or C-terminus of the ED. Generally, fewer than 50 amino acids, more usually fewer than 25 amino acids and preferably fewer than about 15 amino acids will remain joined to the ED after scission of the recognition sequence. However, the fragment that is released should comprise at least about 125 amino acids, more usually at least about 150 amino acids and not more than about 300 amino acids for the independently complexing fragment and may be 500 or more amino acids for the non-independently fusion protein fragments. Stability of the small fragments is greatly enhanced by having a protein that is stable to degradation, which is achieved by having amino acids additional to the ED, particularly the smaller independently complexing EDs. The additional amino acids will usually be added to the terminus of the ED distal to the protease recognition sequence. When there are two EDs on either side of the recognition sequence, long linkers can be employed to provide the stability for the ED, where the linkers may be greater than 50 amino acids, but usually fewer than 100 amino acids. The complex formation inhibiting entities, usually sterically inhibiting entities, may be any moiety that substantially reduces the ability of EA to complex with the ED. Various entities may serve this purpose, including surfaces, liposomes, which includes cells or cell ghosts, and large molecules, that are able to impede the complex formation of ED and EA.

The inhibiting entities will frequently be poly(amino acids) although other chemical moieties may be employed such as polysaccharides or surfaces involving glass, plastic, lipid membranes, etc. The poly(amino acids) may be glycosylated to enhance the steric effect of a sterically hindering entity. The poly(amino acids) may be naturally occurring proteins, mutants of naturally occurring proteins or synthetic proteins, where synthetic proteins means that there is no known naturally occurring analog. Generally the poly(amino acids) will be at least 10 kDa, usually at least about 20 kDa, more usually at least about 25 kDa, and preferably at least about 30 kDa. Since beyond a particular size, there will be no advantage to further increasing the size, where the poly(amino acids) are selected arbitrarily, that is, the poly (amino acid) does not serve a specific protein function, the poly(amino acid) will generally be less than about 125 kDa, usually less than about 100 kDa, and preferably less than about 75 kDa. The molecular weight of a poly(amino acid) hindering entity is not the only consideration, as conformation also has an effect. An extended chain will have less hindering effect than a poly(amino acid) having a globulin formation. At least one of the poly(amino acid) entities will be a naturally occurring protein or fragment thereof, when the recognition sequence is part of the entity.

In many instances, one of the complex inhibiting entities will play a functional role. For example, the poly(amino acid) may comprise the recognition sequence, so that the recognition sequence will be in the proper conformation for cleavage. Alternatively, the poly(amino acid) may undergo self-cleavage when modified, so that the protease assay will detect the modification of the poly(amino acid). Other protease related events that can be measured include complexing to a second protein that makes the recognition sequence available for intermolecular cleavage, activation of a pathway that results in cleavage of the recognition sequence, the presence of a cofactor necessary, directly or indirectly, for cleavage of the recognition sequence, and the like. In effect, any event in the cell where there exists the capability for cleavage of the recognition sequence or the outcome of the event, the capability of cleavage of the recognition sequence can be monitored.

The protein reagent may be primarily comprised of amino acids, amino acids and other common modifiers, such as saccharides, phosphates, lipids, acyl groups, alkyl groups, etc. The protein reagent may also be linked to macromolecules, such as surfaces, e.g. wells, slides, chips, etc., or liposomes, or cells. Generally, only one terminus of the poly(amino acid) will be linked to a surface, except where cells are involved, where a single linkage may be involved or the poly(amino acid) may be threaded repeatedly through the membrane.

The protein reagent, when other than linked to a surface, will generally be at least about 10 kDa and not more than about 500 kDa, usually not more than about 200 kDa, frequently not more than about 150 kDa, usually in the range of about 15 kDa to 100 kDa, more usually in the range of about 15 kDa to 75 kDa for independently complexing enzyme fragments and usually in the range of about 25 kDa to 400 kDa, more usually in the range of about 25 kDa to 250 kDa when comprising non-independently complexing enzyme fragments. When linked to a surface, the protein reagent will be at least about 10 kDa, but usually not more than about 150 kDa for independently complexing enzyme fragments and about 25 to 300 kDa for non-independently complexing enzyme fragments. As previously indicated, the complex inhibiting entities will be chosen so as to substantially interfere with the binding of the EA to the ED, when both hindering entities are present, while there will be significantly less interference when one of the entities has been removed.

While for the most part, the protein reagent can be a single molecule comprised solely of covalent bonds, this is not necessary. For example, one may have a sequence that has an entity that will complex with another protein to provide steric hindrance. One may have biotin or an amino acid equivalent at one terminus of the linker, whereby strept/avidin will serve as a sterically hindering protein. Alternatively, other oligopeptides can serve to bind to antibodies or Fab to provide the sterically hindering protein.

The poly(amino acid) portion of the protein reagent may be linked to a surface by any convenient means. In many cases, the method of linking will depend upon the composition of the poly(amino acid). For example, where there are no available cysteines in the poly(amino acid) portion, then a terminal cysteine can be used to link to an activated olefin, e.g., maleimide, bonded to the surface. Alternatively, one may have a terminal poly(histidine) to complex with complex metal ions, such as nickel, so that a nickel complex on the surface will bind to the poly(histidine). Another technique is to have an amino acid sequence defining an epitope and have antibodies or Fab fragments or their equivalents bound to the surface or analogously, ligand and receptor. In similar vein, amino acid sequences can serve as surrogates for small ligands, such as biotin, so strept/avidin may be bound to a surface for binding such amino acid biotin surrogate, or the like. The particular choice of linkage, whether covalent or non-covalent, will generally not be crucial and will be dictated by the poly(amino acid) portion of the protein reagent, convenience and stability under the conditions of the assay.

For liposomes, one can use various recognition sequences that encode for lipid modification. References illustrative of the different recognition sequences include Magee, et al., Biol Res 2002, 35, 127-31; Kohl, et al., J Biol Chem 2002, 277, 36760-7; Ikezawa, Biol Pharm Bull 2002, 25, 409-17 and Smialowski-Fetter, et al., Eur J Biochem 2002, 269, 1109017. By providing the lipid recognition sequences on one side of the protease recognition sequence distal from the ED, cleavage of the protease recognition sequence will release the ED from the complex inhibiting effect of the liposome.

The preparation of liposomes comprising proteins bound to the outer leaf of the membrane is well established in the literature. See, for example, Willis, et al., Bioconjug Chem 1998, 9, 573-82; Sankaram, Biophys J 1994, 67, 105-12; Radford, et al., Biochem Pharmacol 1991, 41, 307-9; and Claassen and van Rooijen, Prep Biochem 1983, 13, 167-74.

As indicated, when a hindering entity is a surface, one can obtain sufficient differentiation between ED bound to the surface and ED released from the surface in the affinity for the EA. Therefore, it is possible to have a single hindering entity, where the ED is linked to the hindering surface through the recognition sequence. Further hindrance is achieved with the second hindering entity.

The recognition sequence will normally be linked to the surface or liposome by a poly(amino acid) sequence of at least about 10 amino acids, more usually at least about 25 amino acids and not more than about 150 amino acids, usually not more than about 100 amino acids. The length of the chain will be governed by the inhibition of the surface or liposome to inhibit protease cleavage, where the shortest chain providing the desired characteristic will generally be the most convenient. When the linker is a protein that passes through the membrane repeatedly, only the linking group to the first membrane bound sequence is counted. Also, depending upon the nature of the surface, the surface may have a functionality for linking which is tethered by other than a poly(amino acid) chain, so that the length of this chain will affect what minimum length of chain is required for the protein reagent.

The protein reagent may be present intracellularly, in a lysate or in a sample composition. The protein reagent, when a poly(amino acid) backbone, can be prepared by the expression of a gene encoding the protein reagent. By introducing an expression construct containing the gene encoding the protein reagent into an appropriate host, the protein reagent will be expressed and available for the protease measurement. The protease measurement may be in relation to an event in the cell that activates the protease of interest, the expression of the protease, a change in the environment that results in the expression, activation or deactivation of the protease, the presence of a gene in the host that is activated to express a protein that results in a change in the activity of the protease of interest, the production or destruction of a cofactor that affects the activity of the protease of interest, or the like. Therefore, many different events may be of interest that affect the protease of interest, allowing for an indirect measurement of the event. Thus, candidate compounds may be studied for their activity where the readout is a change in activity of the protease of interest. While in some instances, the result may be ambiguous as to the manner in which the compound is acting, the observed change in the activity of the protease of interest indicates that the candidate compound directly or indirectly affects the protease activity in the cell.

The subject method may be performed intracellularly or extracellularly, in the latter case with a lysate, a lysate enriched for one or more components, a lysate fraction, substantially pure protein reagent or a mixture of protein reagents, or the like. In the case of the intracellular assay, the expression construct comprising the gene encoding the protein reagent will be present or introduced into a host cell. The expression may be constitutive or inducible, depending upon the promoter employed for initiating transcription. The expression construct may be integrated into the genome of the host or be present on an extrachromosomal element, either stably or transiently present in the host. Numerous vectors based on origins of replication or viral origins are commercially available and may be used in the present invention. Once expression occurs, the assay may then be performed by providing for the expression of EA in the host cell and introducing a non-limiting amount of substrate or lysing the cells at a single time point or a plurality of time points and adding EA and substrate to the lysate. In some instances, it may be desirable to enrich the lysate for the protease, the protein reagent or other component, where such enrichment may involve the use of antibodies to remove undesirable components in the lysate, chromatography, or other separation that does not inactivate the protease and desirably not denature the protein reagent.

Alternatively, one may wish to perform a protease assay with pure or impure samples of the protein reagent and the protease, where the individual reactive component of the assay medium is at least about 0.1 weight % of total protein and may be at least about 1 weight % or higher. In some instances, one may be interested in a mixture of protein reagents, where one is interested in the effect of the presence of different proteins on the protease action with the protein reagent. Where a number of different proteins share the same recognition sequence, one can determine the susceptibility of the different proteins to the protease, by measuring the total reaction and then deconvoluting using antibodies to the two proteins of the protein reagent. By having a capturing antibody that is retained with the ED and a labeled detection antibody, one can determine for each protein reagent, the amount of the protein reagent that has been cleaved. In this way, one may determine a hierarchy as to the susceptibility for the different proteins to protease cleavage. In the presence of a limiting amount of protease, by taking aliquots of the sample and analyzing for total cleavage and cleavage as to one or more of the protein reagents, the rate of cleavage of each of the protein reagents in the presence of the other protein reagents can be determined. Those protein reagents bound to surfaces or liposomes find particular application in these assays.

The target proteases of interest are for the most part those that have specific recognition sequences, preferably having at least about 3 amino acids as their recognition sequence and usually not more than about 12 amino acids, although additional amino acids may be involved in enhancing the recognition by the protease. As indicated, the protease may be an intra- or intermolecular protease, where in the former case, the protease will require activation before self-cleavage. Enzymes of interest include serine/threonine hydrolases, cysteine hydrolases, metalloproteases, BACEs (e.g., α-, β- and γ-secretases). Included within these classes are such protein groups as caspases, the individual MMPs, elastases, collagenases, ACEs, carboxypeptidases, blood clotting related enzymes, complement components, cathepsins, dipeptidyl peptidases, granzymes, etc. For other enzyme groups, see Handbook of Proteolytic enzymes, ed. A J Barnet, N D Rowland, and J F Woessner. Other types of enzymes include abzymes.

Specific serine proteases include neutrophil elastase, involved in pulmonary emphysema, leukocyte elastase, tyrosine carboxypeptidase, lysosomal carboxypeptidase C, thrombin, plasmin, dipeptidyl peptidase IV; metalloproteinases include carboxypeptidases A and B, angiotensin converting enzyme, involved in hypertension, stromelysin, involved with inflammatory disorders, e.g., rheumatoid arthritis, *P. aeruginosa* elastase, involved in lung infections; aspartic proteases include renin, involved in hypertension, cathepsin D, HIV protease; cysteine proteases include lysosomal carboxypeptidase, cathepsin B, involved in cell proliferative disorders, cathepsin G, cathepsin L, calpain, involved with brain cell destruction during stroke; etc.

The proteases may be involved with various processes, such as infections and replication of the infectious agent, viral, bacterial, fungal, and protista; phagocytosis, fibrinolysis, blood clotting cascases, complement cascades, caspase cascades, activation of proforms of proteins, protein degradation, e.g., ubiquitinated proteins, apoptosis, etc., cell growth, attachment, synaptic processes, etc. The proteases may come from a variety of sources, either prokaryotes, eukaryotes or viruses, depending on the nature of the assay. For detection of infectious diseases, the source of the protease may be a virus, a bacterium, protista, fungus or other unicellular organism. For higher orders of species, the enzyme may be derived from plants, non-vertebrates, vertebrates, particularly mammals, such as domestic animals, e.g., bovine, porcine, canine, feline, lagomorpha, murine, etc., primates, e.g., humans. The purpose of measuring the protease will be widely varied. In some instances, one will be concerned with identifying the source, such as a virus, where the protein reagent will comprise a viral protein specifically cleaved by the protease. In other cases, one may be interested in the presence of the protease in a biological sample, determining whether the protease is present and in what concentration. One will also be interested in determining the amount or change in amount of protease in response to changes in the nature of the cell, e.g., normal and cancerous, or in response to a change in environment, e.g., physical or chemical environment, native or diseased state, e.g., infection, or the like. The subject system is particularly useful for high throughput screening of drug candidates, as to their effect on the target protease or non-target proteases.

As already indicated, the organisms from which the proteases are naturally derived are varied. Among viruses, the proteases may be derived from HIV-1, and -2, adenovirus, hepatitis viruses, A, B, C, D and E, rhinoviruses, herpes viruses, e.g., cytomegalovirus, picomaviruses, etc. Among unicellular microorganisms are Listeria, Clostridium, Escherichia, Micrococcus, Chlamydia, Giardia, Streptococcus, Pseudomonas, etc. Of course, as indicated above, there are numerous mammalian proteases of interest, particularly human proteases.

Depending on the target protease to be measured, one of the proteins linked to the ED may be defined. Where the recognition sequence is dependent on the conformation of the protein, it will usually be necessary to use at least a portion of the natural protein to obtain the desired conformation. Where one is interested in a modification of the protein that permits inter- or intercellular proteolysis, the protein will also be defined. Where the recognition sequence is not dependent on the natural conformation, one may then use the recognition sequence linked to the ED and joined at the other terminus to an arbitrary protein that does not interfere with the protease hydrolysis of the recognition sequence. Therefore, the protein associated with the recognition sequence will be widely varied, being either specific for the protease being measured or being arbitrary and joined to the recognition sequence to provide the inhibition of binding of the EA to the ED.

There are numerous scientific articles describing proteases and their substrates. Illustrative articles are as follows, whose relevant content is specifically incorporated herein by reference. Among the metalloproteinases are MMP-2, having target sequences L/IXXXHy; XHySXL; and HXXXHy (where Hy intends a hydrophobic residue), Chen, et al., J. Biol. Chem., 2001. Other enzymes include mitochondrial processing peptidase, having the target sequence RXXAr (where Ar is an aromatic amino acid), Taylor, et al., Structure 2001,9, 615-25; caspases, VAD, DEVD (SEQ ID NO: 7) and DXXD, as well as the RB protein, Fattman, et al., Oncogene 2001, 20, 2918-26, DDVD (SEQ ID NO: 8) of HPK-1, Chen, et al., Oncogene 1999, 18, 7370-7; VEMD/A and EVQD/G of Keratins 15 and 17, Badock, et al., Cell Death Differ. 2001, 8, 308-15; WEHD (SEQ ID NO: 9) of pro-interleukin -1βRano, et al., Chem. Biol. 1997, 4,149-55; furin, KKRKRR (SEQ ID NO: 10) of RSV fusion protein, Zinimer, et al., J. Biol. Chem.2001, 20, 2918-26; HIV-1 protease, GSGIF*LETSL (SEQ ID NO: 11), Beck, et al., Virology 2000, 274, 391-401. Other enzymes include thrombin, VPRGS (SEQ ID NO: 12), Factor Xa protease, IEGR (SEQ ID NO: 13), enterokinase, DDDDK (SEQ ID NO: 14), 3C human rhinovirus protease, LEVLFQ/GP (SEQ ID NO: 15).

Other references describing proteases include: Rabay, G. ed., "Proteinases and Their Inhibitors in Cells and Tissues, 1989, Gustav Fischer Verlag, Stuttgart; Powers, et al., in "Proteases—Structures, Mechanism and Inhibitors," 1993, Birkhauser Verlag, Basel, pp.3-17; Patick and Potts, Clin. Microbiol. Rev. 1998, 11, 614-27; Dery, et al., Am. J. Physiol. 1998, 274, C1429-52; Kyozuka, et al., Cell Calcium 1998, 23, 123-30; Howells, et al., Br. J. Haematol. 1998, 101, 1-9; Hill and Phylip, Adv. Exp. Med. Biol. 1998, 436, 441-4; Kidd, Ann. Rev. Physiol. 1998, 60, 533-73; Matsushita, et al., Curr. Opin. Immunol. 1998, 10, 29-35; Pallen and Wren, Mol. Microbiol.1997, 26, 209-21; DeClerk, et al., Adv. Exp. Med. Biol. 1998, 425, 89-97; Thomberry, Br. Med. Bull. 1997, 53, 478-90, which references are specifically incorporated herein.

Besides the naturally occurring recognition sequences, using combinatorial approaches, one can design recognition sequences that will be specific for one or a family of enzymes. By preparing a library of oligopeptides that are labeled and having an array of the labeled oligopeptides where the location identifies the sequence, one need only add the protease of interest to the array and detect the release of the label. Having microwell plates, with the oligopeptides bound to the surface and labeled with a fluorescer, allows one to follow cleavage by internal reflection of activating irradiation. Numerous other approaches can also be used. By using synthetic sequences, one can optimize the cleavage for a particular protease. By using a plurality of protein reagents, one can obtain profiles that will be specific for specific enzymes.

Proteins can find use as part of the protein reagent that are not specific for the protease, but have the desired stability in a cell in that they are not readily degraded, provide solubility, are substantially free from adverse interactions with other proteins in the cell.

The protein reagent will usually be prepared by expression of a gene encoding the protein reagent. An expression construct is prepared having a transcriptional and translational regulatory region, which may include an enhancer that will be functional in the host cell. Where one is interested in the protein reagent for use in vitro, the host will be selected primarily for convenience as to expression and purification. For the most part, unicellular hosts, such as bacteria and yeast, will be employed. If glycosylation is desired, one will usually use a mammalian host cell that provides for glycosylation, particularly the natural glycosylation associated with the protein undergoing cleavage of the protein reagent. The expression construct is produced in accordance with conventional ways, as described in various laboratory manuals and by suppliers of vectors that are functional in numerous hosts. See, for example, Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Vectors that may be used include viruses, plasmids, cosmids, phagemids, YAC, BAC and HAC. Other components of the vector may include origins of replication for one or more hosts, expression constructs for selection, including antibiotic resistance, proteins providing for a signal, etc., integration sequences and enzymes providing for the integration, multiple cloning sites, expression regulatory sequences, expression construct for a protein of interest, particularly where the protein is coordinately or differentially expressed in relation to the protein reagent, sequences allowing for ready isolation of the vector, etc. Commercially available vectors have many or all of these capabilities and may be used to advantage.

The DNA or RNA vectors may be introduced into a cellular host, whereby the expression of the protein reagent can occur. The host may be a primary cell, a cell line, a unicellular microorganism, or the like, where the cell may be modified having an expression construct integrated or transiently present in the cell expressing EA, expressing or overexpressing a protein that the cell does not normally express under the conditions of the assay, not expressing a protein that the cell normally expresses as a result of a knockout, transcription or translation inhibitor, or the like.

The gene encoding the protein reagent will be part of an expression construct. The gene is positioned to be under transcriptional and translational regulatory regions functional in the cellular host. In many instances, the regulatory regions may be the native regulatory regions of the gene encoding the protein of interest, where the protein reagent may replace the native gene, particularly where the protein reagent is functional as the native protein, may be in addition to the native protein, either integrated in the host cell genome or non-integrated, e.g., on an extrachromosomal element. In those cells in which the native protein is present and expressed, the protein reagent will be competing with the native protein for transcription factors for expression. The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the protein of interest, which gene will not interfere significantly with the transcription of the protein reagent. However, where one is interested in the transcription of the gene of interest, that is, proteins involved in controlling the induction and transcription of the protein of interest, it will usually be desirable to use the native transcriptional regulatory region.

It should be understood that the site of integration of the expression construct, if integrated into a host chromosome, would affect the efficiency of transcription and, therefore, expression of the protein reagent. One may optimize the efficiency of expression by selecting for cells having a high rate of transcription, one can modify the expression construct by having the expression construct joined to a gene that can be amplified and coamplifies the expression construct, e.g., DHFR in the presence of methotrexate, or one may use homologous recombination to ensure that the site of integration provides for efficient transcription. By inserting an insertion element into the genome, such as Cre-Lox at a site of efficient transcription, one can direct the expression construct to the same site. In any event, one will usually compare the enzyme activity from cells in a predetermined environment to cells in the environment being evaluated.

The vector may be introduced into the host cells by any convenient and efficient means, such as transfection, electroporation, lipofection, fusion, transformation, calcium precipitated DNA, etc. The manner in which the vector is introduced into the host cells will be one of efficiency and convenience in light of the nature of the host cell and the vector and the literature has numerous directions for the introduction of a vector into a host cell and the selection of the host cells that have effectively received the vector. By employing expression constructs that allow for selection, e.g., antibiotics, the cells may be grown in a selective medium, where only the cells comprising the vector will survive.

Once the host cells have been transformed and comprise the vector and are expressing the protein reagent, the cells may be used in a variety of ways. Where the protein of interest is an endogenous protein, when the cell has EA and a substrate that produces a detectable signal, one may measure the signal from the culture medium. Alternatively, one can use such devices as a fluorescence activated cell sorter, where the signal is fluorescence, or other method for measurement. Where one needs to add the necessary β-galactosidase reagents for the β-galactosidase reaction, the cells are lysed and the necessary reagents added and the signal determined. The cells may be grown under conditions that affect the protease of interest, for example, inhibiting transcription, translation or the protease activity. By introducing compounds that may serve as agonists or antagonists of the protease of interest, one can measure the rate at which the protein reagent is cleaved by the increase in activity of the β-galactosidase. By taking a determination at a specific time or at two or more different times, one can measure the rate of the β-galactosidase reaction. By comparing cells in the presence and absence of the candidate compound, one can determine the effect of the candidate compound on the protease activity.

Expression vectors containing the protein reagent gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of the protein reagent gene inserted in an expression vector can be detected by nucleic acid hybridization using probes comprising sequences that are homologous to the protein reagent gene. hi the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors can be identified by assaying for the activity of the protein reagent gene product expressed by the recombinant expression vector.

One may use promoters that are active for a short time, such as viral promoters for early genes, for example, the human cytomegalovirus (CMV) immediate early promoter. Other viral promoters include, but are not limited to, strong promoters, such as cytomegaloviral promoters (CMV), SR.alpha. (Takebe et al., Mole. Cell. Biol. 8:466 (1988)), SV40 promoters, respiratory syncytial viral promoters (RSV), thymidine kinase (TK), beta-globin, etc. Alternatively, an inducible promoter can be used.

A large number of promoters have found use in various situations, for various purposes and for various hosts. Many promoters are commercially available today. Expression of the protein reagent may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122); immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444); mouse mammary tumor virus control region which is active in testicular, breast, lymphoid and mast cells (Leder et al., 1986, Cell 45:485-495): albumin gene control region which is active in liver (Pinkert et al., 1987, Genes and Devel. 1:268-276); alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171); beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987; Cell 48:703-712); myosin light chain-2 gene control region which is active in skeletal muscle (Sani, 1985, Nature 314:283-286); prostate specific antigen control region, which is active in prostate cells (U.S. Pat. Nos. 6,197,293 and 6,136,792); and gonadotropic releasing hormone gene control region which is active in the hypothalamus (Mason et al., 1986, Science 234:1372-1378). Alternatively, expression of the protein reagent gene can be under control of an inducible promoter, such as metallothionein promoter, which is induced by exposure to heavy metals. For control of the gene transfected into certain brain cells, a glucocorticoid inducible promoter can be used, since glucocorticoids can cross the blood-brain barrier. Alternatively, an estrogen-inducible promoter, which would be active in the hypothalamus and other areas responsive to estrogen, can be used. The present invention contemplates the use of any promoter inducible by a pharmacologic agent that can cross or transmit a signal across the membrane and for neuronal cells, the blood-brain barrier and influence transcription.

Vectors containing DNA encoding the following proteins, for example, have been deposited with the American Type Culture Collection (ATCC) of Rockville, MD: Factor VIII (pSP64-VIII, ATCC No. 39812); a Factor VIII analog, "LA", lacking 581 amino acids (pDGR-2, ATCC No. 53100; VWF (pMT2-VWF, ATCC No. 67122); EPO (pRK1-4, ATCC No. 39940; pdBPVMMTneo 342-12 (BPV-type vector) ATCC No. 37224); and GM-CSF (pCSF-1, ATCC No. 39754).

The vector will include the fusion gene under the transcriptional and translational control of a promoter, usually a promoter/enhancer region, optionally a replication initiation region to be replication competent, a marker for selection, as described above, and may include additional features, such as restriction sites, PCR initiation sites, an expression construct providing constitutive or inducible expression of EA, or the like. As described above, there are numerous vectors available providing for numerous different approaches for the expression of the protein reagent in a host.

The host cells will be selected to provide the necessary transcription factors for expression of the protein reagent and the other components for the purposes of determination. The host cells will also be selected toward providing an environment resembling the environment being simulated. hi many cases, primary cells may be employed, both those maintained in culture and obtained directly from a patient. However, in many other cases, established cell lines will be used, since the cell lines can provide the desired environment and allow for direct comparisons between studies, which comparisons may not be available where using primary cell lines from patients.

The efficiency of transcription can also be determined by using a protein reagent that is stable, i.e., it is not subject to significant modification during the period of the assay. By using a stable protein, such as a prion, β-amyloid, synthetic polypeptides, such as using collagen, keratin or elastin motifs, or providing for secretion into a non-proteolytic environment, one can determine the rate of expression from a regulatory region of interest. By using homologous recombination, one can insert the protein reagent to be under the regulatory control of the regulatory region of interest, including promoters, enhancers, etc. Alternatively, one may introduce a construct with the appropriate regulatory region, where the native and constructed expression systems would both be active, while the protein reagent would indicate the effectiveness of the expression system. In this instance, one would usually be interested in the effect of a change, e.g., environment, genome, etc., on the transcriptional activity of the regulatory region. One could then evaluate the effect of an agent on the transduction of a signal as a result of a binding event at the cell surface, the effect of an intracellular inhibitor, or the effect of a second pathway that involves a first pathway. Desirably, the protein reagent would replace one of the copies of the natural gene, so as to have the same environment for transcription.

When using β-galactosidase as the enzyme, a number of substrates for β-galactosidase are known, where the product is fluorescent or emits light. The common substrates are β-D-galactopyranosyl phenols, such as fluorescein, mono- and di-substituted, o-nitrophenyl-β-D-galactoside, β-methylumbelliferyl-β-D-galactoside, X-gal, resorufin-β-D-galactoside, commercially available oxetanes, e.g.,Galacto-Light Plus® kits (chemiluminescence) and chlorophenol red. The di-β-D-galactopyranosylfluorescein, and chlorophenol red-β-D-galactopyranoside may be used as intracellular markers.

The simplest procedure to describe is the use of cells in culture and analysis of the lysate. In this case, the cells are grown in culture. The protein reagent and other constructs, as appropriate, may be present in the cell integrated into the genome or may be added transiently by the various methods for introducing DNA into a cell for functional translation. The cells may be in culture or in vivo. These methods are amply exemplified in the literature, as previously described. By employing a marker with the protein reagent for selection of cells comprising the construct, such as antibiotic resistance, development of a detectable signal, etc., cells in culture comprising the protein reagent can be separated from cells in which the construct is absent. Once the protein reagent is being expressed, the environment of the cells may be modified, if desired. Candidate compounds may be added, ligand for receptors, surface membrane or nuclear, or the two of these may be added in combination, changes in the culture medium may be created, other cells may be added for secretion of factors or binding to the transformed cells, viruses may be added, or the like. Given sufficient time for the environment to take effect and/or taking aliquots of the culture at different time intervals, the cells may be lysed with a lysis cocktail comprising EA and enzyme substrate and the signal from the product read. One can then relate this result to the amount of protein reagent present, particularly by using standards where the lysate is spiked with different amounts of the protein reagent and the amount of active protein reagent determined. One would then have a graph relating signal to amount of active protein reagent in the lysate.

For convenience, kits can be provided that may include all or some of the major components of the assays. For example, a kit may include an expression construct, by itself or as part of a vector, e.g., plasmid, virus, usually attenuated, where the expression construct may include a marker, a gene encoding a protein for integration, a replication initiation site, and the like. In addition to the expression construct, the kit may include EA, substrate for β-galactosidase, one or more cell lines or primary cells, a graph of response in relation to the amount of ED present, buffer, etc. In some instances, cells may be engineered to provide a desired environment, such as high levels of expression of a protein involved in a pathway of interest, such as surface membrane receptors, GPCRs, nuclear receptors, e.g., steroid receptors, transcription factors, etc., or may have been mutated, so as to have reduced levels of expression affecting the expression of the protein reagent and one is interested in enhancing the level of expression.

As indicated, the subject method can be used in a variety of situations to great effect, since the ED is small enough to allow for functioning of the protein of interest as a protein reagent with ED, while allowing for ED to complex with EA to provide a functional β-galactosidase.

The following examples are intended to illustrate but not limit the invention.

EXPERIMENTAL

In order to demonstrate the subject invention, the DNA sequences of ED (also referred to as ProLabel) and Interleukin-4 (IL4) are molecularly cloned into a glutathione-S-Transferase (GST) fusion protein expression vector (pGEX6P-1) where the fusion: GST-ED-IL4 protein is expressed in bacterial cells. By expressing proteins flanking both the $NH_2$ and COOH-terminal ends of ED, the ability of ED to complement with EA is substantially reduced. Cleavage of the GST moiety from the purified fusion protein results in substantially increased complementation activity.

Figure 3A:
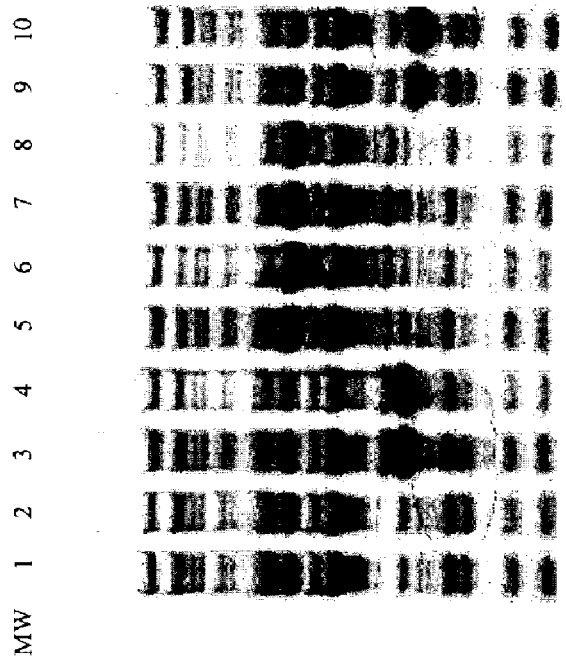
FIG. 3A shows pGEX-ED-IL4 clones in MC 1061 cells.
Figure 3B:
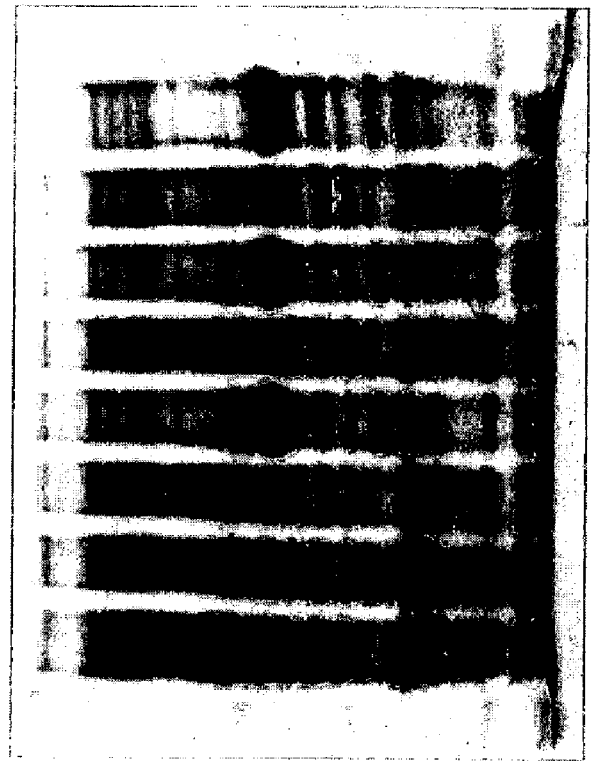
FIG. 3B shows pGEX-ED-IL4 clones in BW 26444 cells.
Figure 5B:
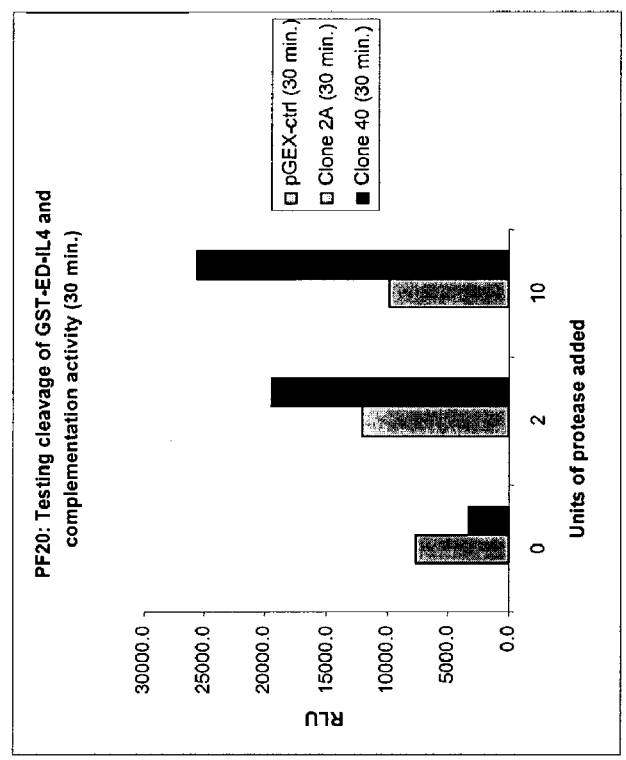
FIG. 5 demonstrates EFC activity of the GST-ED-IL4 construct after addition of increasing amounts of a specific protease at 15 min (FIG. 5A) and at 30 min (FIG. 5B) read times.
Figure 5A:
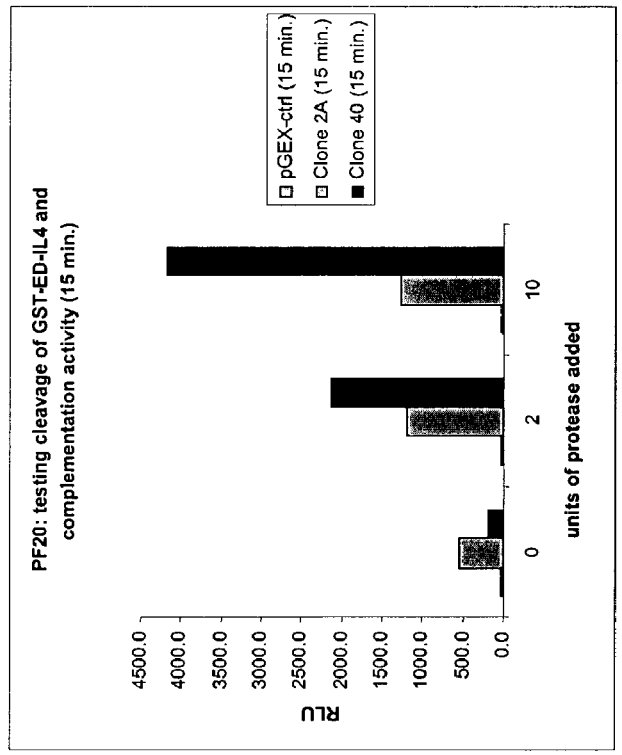

1. Generated by PCR, a 600 base pair Bam HI/Bam HI fragment to ED-IL4, using DNA from plasmid pQE30-ED-IL4 generated by DiscoveRx, Corp as the template. The sequence of the fragment (Seq. ID: No. 1) is shown in FIG. 1.
2. The following primers were used:
   a) B-ED-f: 5'-CACGGATCCAGCTCCAATTCACTG-GCCGTCG-3' (Seq. ID: No.2)
   b) BH-IL4-R: 5'-CGCGGATCCAAGCTTTCAGCTCGAA-CACTTTGAATA-3' (Seq. ID: No. 3)
3. The generated PCR fragment was digested with Bam HI restriction enzyme following standard protocols and then gel-purified.
4. The DNA was recovered from the gel slice by using a Qiagen Gel extraction kit.
5. The Bam HI fragment was then ligated with gel purified pGEX 6P-1 plasmid (Amersham Pharmacia Biotechnology) DNA that had also been digested with Bam HI and gel purified following the same methods.
6. Ligation was performed using New England Biolabs Quick Ligation kit following the protocol. Half of the ligation mix was used to transform DH5α cells. The transformation mix was plated on LB ampicillin plates and potential transformants were selected and plasmid DNA was isolated and digested with a series of restriction enzymes to confirm the cloning reaction (see FIG. 2; Protein Seq. ID: No. 4 and DNA Seq. ID: No. 5).
7. Transform MC1061 cells (see FIG. 3A) and BW26444 cells (see FIG. 3B) with the GST-ED-IL4 plasmid clone. Examine expression of the fusion protein product after induction with 0.1 mM IPTG. Total cellular protein displayed by Coomassie blue staining.
8. Confirmed by western blot analysis using both anti-GST polyclonal antibody and an anti-hIL4 antibody that clones #2 and #40A and #40B are expressing the GST-ED-IL4 fusion protein of predicted size.
9. Testing for complementation activity of the purified GST-ED-IL4 fusion protein after treatment with a sequence specific protease (PRE-SCISSION™ protease) that cleaves the GST moiety from the fusion protein.
   Control (pGEX plasmid vector) and test (ED-IL4 clones) were grown overnight in L-broth with 50 μg/mL ampicillin. The next day, the cultures are used to inoculate duplicate 3 mL tubes with fresh L-Broth with ampicillin. The cultures are allowed to go for 3 hours (~$OD_{600}$ reading of 0.2-0.3). Induction of the fusion is done by adding 100 mM IPTG to 0.1 mM for one sample set of each culture being tested. The cultures are allowed to go for another 2 hours at 37° C. After this time, the cultures are collected by centrifugation, the cell pellet is resuspended in 1 mL PBS+a protease inhibitor (PI) cocktail. The resuspended cells are then sonicated two times for 30 seconds with a one minute interval on ice between sonications. The lysate is clarified with a low speed spin. The supernatant is removed and to this, 300 μL of GST-agarose resin is added. The mixture is incubated at 4° C., rocking for 2 hours. After this time, the resin is pelleted, washed four times with PBS+PI. Next, the fusion protein is eluted from the resin with the addition of 250 μL of 20 mM reduced glutathione. This mixture is allowed to rock at 4° C. for 1 hour. The resin is again pelleted and the supernant is retained for analysis. 0, 2 or 10 units of protease is add to 50 μL of the eluted fusion protein and incubated for 4 hours at 4° C. 15 μL of the treated sample is then transferred in triplicate to a well on a 384-well plate. To this, 15 μL of 1×EA is added and 20 μL of chemiluminescent substrate is added. The samples are read on a Packard lumicount reader immediately and for 15 minute intervals thereafter for the next hour. See FIG. 4.
10. To determine specificity of the cleavage event, the eluted GST-ED-IL4 material is treated again with 0, 1 or 3 μL of the pre-scission protease (2 mg/mL) or 1 or 3 μL of Caspase 3 enzyme (7.3 μg/mL). The samples are treated for 4.5 hours at 4° C. 15 μL of 1×EA is added and 20 μL of chemiluminescent substrate is added. The samples are read on a Packard lumicount reader immediately and for 15 minute intervals for the next hour. See FIGS. 5A and 5B.
1. Materials:
HEK293 parental cell line
HEK293 IκB-β-galactosidase ED (55 mer) stable transfectant.
Growth media (DMEM/10% FBS).
Factor Xa, 1 μg/μL stock in water, kept as a −80° C. stock (Roche, Cat. no. 1 585 924)
Factor Xa cleavage buffer, made by adding 10 mg/mL BSA to 0.1 mg/ml final concentration (New England Biolabs) and 0.5 parts 0.2M $CaCl_2$ to 98.5 parts Dulbecco's PBS (Sigma Cat. no. D8537) BSA is added just prior to use,
EA core buffer (PIPES, 30.24 g/L; NaCl, 23.38 g/L; EGTA, 3.80 g/L; Mg acetate, 2.15 g/L; Tween, 0.5 mL; NaOH, 6.9 g/l ; $NaN_3$, 0.95 g/L, pH 6.9

Figure 6A:
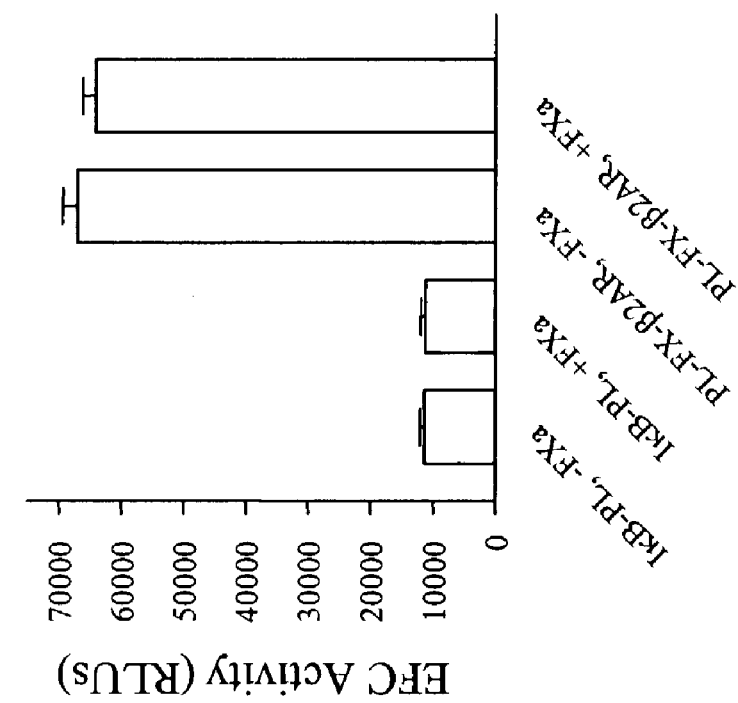
FIG. 6 shows bar graphs showing the results of assays employing a supernatant fraction (FIG. 6A) and an adherent fraction (FIG. 6B), where the former is not lysed and the latter is lysed.
Figure 6B:
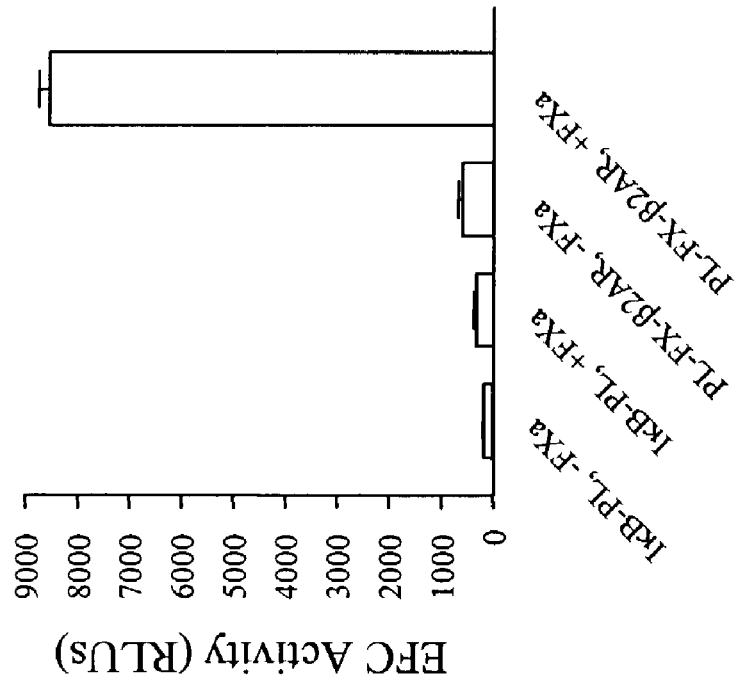

EA reagent (1.8 μM in EA core buffer)
Cell lysis buffer ($KH_2PO_4$, 0.6805 g/L; $K_2HPO_4$, 0.8709 g/l ; NaCl, 0.5844 g/L; CHAPS, 10 g/L; pH 6.9 with NaOH)
Chemiluminescent substrate (Tropix, Applied Biosystems Inc.)+Gal-Star+Emerald Enhancer
Plasmid pPL-FXa-$β_2$-AR (or pPL (ED)-FXa (FXa cleavage consensus sequence)-$β_2$-adrenergic receptor (b2-AR))
FuGene 6 transfection reagent (Roche Cat. no. 1 815 091)
2. A construct, named pPL-FX-b2AR, was prepared as follows. First, pCMV-PL-N1, a mammalian expression vector for creating N-terminal ED fusion proteins, was created by precise replacement of the EGFP coding sequences in pEGFP-C1 (Clontech) with sequences encoding ED. Next, a XhoI/BamHI DNA fragment encoding the FXa cleavage site followed by the b2AR was sub cloned into the XhoI/BamHI sites of pCMV-PL-N1, creating a fusion of ED-FXa-b2AR. The FXa-b2AR DNA fragment was obtained by PCR amplification from a b2AR DNA template using PCR primers that introduced a XhoI site and FXa cleavage site encoding sequences at the 5' end, and a BamHI site at the 3' end. The sequence is described subsequently as SEQ ID:NO. 6, except that GST is present at one terminus.
3. Procedure:
4. In this study, the assay procedure was as follows: HEK293 transfectant cells expressing either the cytoplasmic protein IκB-PL (stable transfectant) or PL-FXa-b2AR (transient transfectant) were seeded into two wells each of a 6-well culture dish at a density that gave ~80% confluency following 2 days growth. For transfection, transfection mix was prepared according to the supplier FUGENE, using 0.15 μL FUGENE reagent, 0.05 μg DNA and 5 μL serum free media. The transfected cells were grown in DMEM/10% FBS media for 48 to 72 hours prior to assay.
5. At this time, culture media above the cells was removed by gentle aspiration. To one set of wells was added 1.0 mL of FXa buffer composed of PBSC/BSA containing 2 μg/mL FXa. To the other was added the same buffer lacking FXa. Reactions were incubated at room temperature for 1 hour. Liquid above the cells (the supernatant fraction) was carefully collected by pipetting and then transferred to individual microfuge tubes. The supernatants were cleared of any cells that might have been carried over in the transfer by two sequential, gentle centrifugations. Fifty microliters of each supernatant fraction was aliquoted in quadruplicate to individual wells of a 96-well assay plate. To these wells was added 80 μL of EA Core Buffer/EA Reagent (3:1). To the cells remaining in the culture wells (the adherent cell fraction) was added 1 mL of PBSC/BSA followed by 1.6 mL of Cell Lysis Buffer/EA Reagent (3:1). The cells were lysed in this solution by pipetting up and down and then 130 μL of each sample was aliquoted in quadruplicate to individual wells of the 96-well assay plate. The assay plate was incubated at 37° C. for 1 hour, after which 30 μL of CL substrate was added per well. The plate was incubated at room temperature protected from light and readings were taken periodically on the Northstar plate reader from 15 minutes to 1 hour following substrate addition. See FIGS. 6A and 6B for results.
6. That Factor Xa does not cause cell lysis was established by an experiment in which a 96-well microtiter plate is seeded 100 μL/well with two cell lines: a HEK293 IκB-β-galactosidase ED (55 mer) stable transfectant and the HEK293 parental cell line transiently transfected with plasmid pPL-FXa-β₂-AR. HEK293 IκB-β-galactosidase ED (55 mer) stable transfectant cells were obtained from a stock plate (~50% confluent) treated with trypsin, quenched with media, centrifuged and resuspended in 6 ml fresh media. The suspension for seeding the microtiter plate was 0.764 mL washed cell suspension and 3.23 mL of fresh media. 100 µL aliquots were transferred to the microtiter plate wells, 4 columns by 8 rows. The HEK293 parental cell line transfected with pPL-FXa-β₂-AR was treated as above, except that the parental cell line was ~90% confluent and 4.2 mls of the washed cell suspension was diluted with 17.8 mL of media. For transfection, transfection mix was prepared according to the supplier FuGENE, using 0.15 µL FuGENE reagent, 0.05 µg DNA and 5 µL serum free media.

Figure 7:
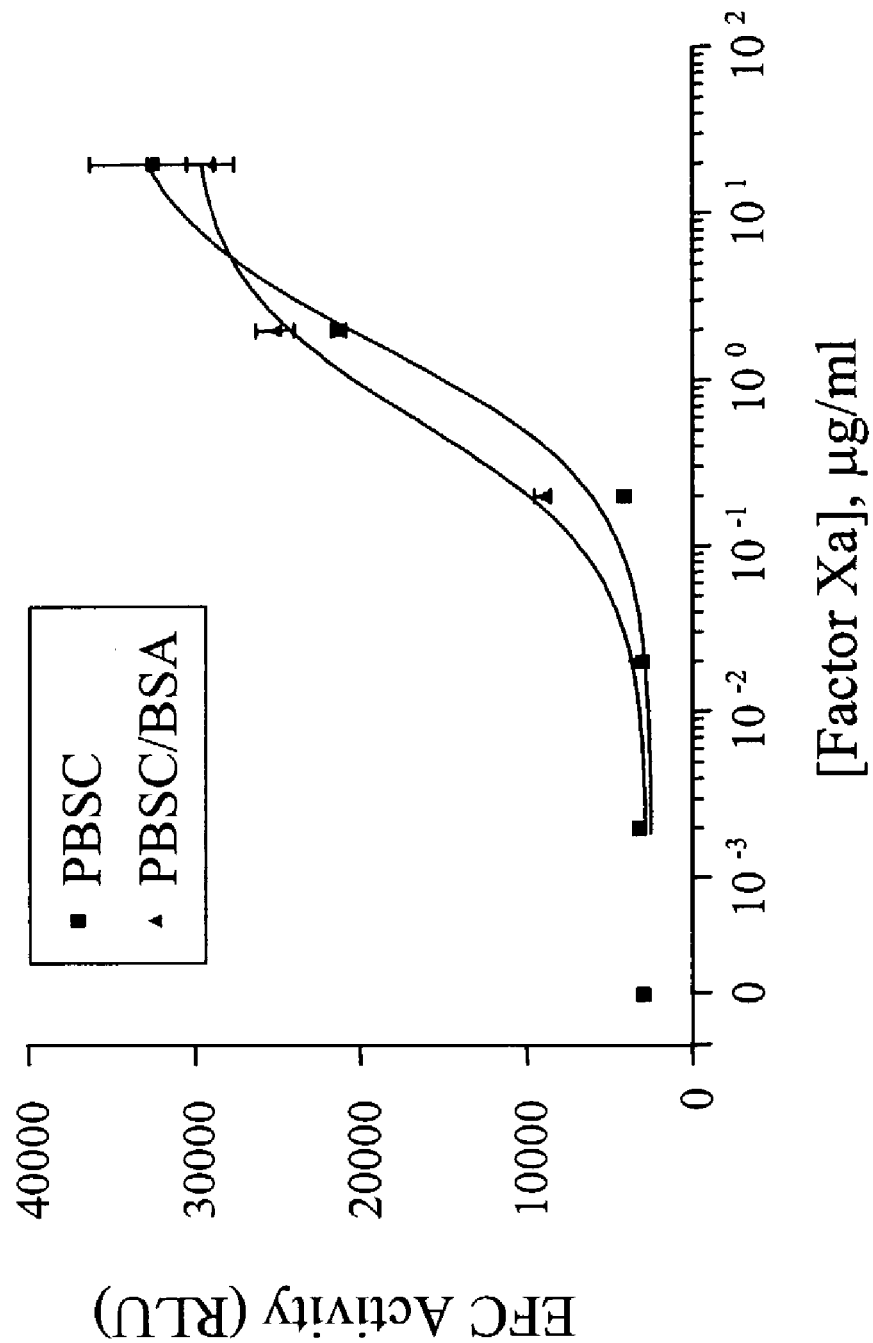
FIG. 7 is a plot of the effect of FXa concentration on the observed signal in two different buffers with an expression construct comprising ProLabel (ED)

7. After seeding the wells, the cells were allowed to grow ~2 days to ~80% confluence. Serial dilutions of the FXa solution were made and the dilutions added as 50 µL to separate wells of the different HEK293 cells that had their growth media removed by aspiration.
8. The mixtures were then incubated for 1 h 10 min at room temperature. To the treated mixtures were added 80 µL of EA Core Buffer/EA Reagent (3:1) to each well (whole-cell assay). To a replica set of mixtures that were not treated with Factor Xa was added 80 µL Cell Lysis Buffer/EA Reagent (3:1) per well (lysed-cell assay). The plate was gently agitated to facilitate mixing of the reagents and then incubated at 37° C./5% $CO_2$ for 1 h. Chemiluminescent substrate (30 µL) was added to each well, followed by gentle agitation and incubation in the dark at room temperature for 15 min prior to a 90 sec reading taken with a Northstar plate reader. After adjusting the results for whole-cell values as compared to lysed-cell values, the data were graphed showing that for the IκB-β-galactosidase ED stable transfectant cells there was substantially no change in the readings with variation in the concentration of Factor Xa, while the pPL-FXa-β₂-AR transient transfectant cells showed an increase in the readings from 0.01 ng/well to 1000 ng/well of Factor Xa. The results are shown in FIG. 7.
9. The assay compared the effect of FXa enzyme concentration on the EFC (enzyme fragment complementation with formation of β-galactosidase) activity as observed with relative luminescent units (RLU). Using either PBSC or PBSC/BSA (0.1%) buffer, a difference in about 30,000 RLUs was observed over a range in concentration of FXa of about $10^{-3}$ to $10^1$ µg/mL.
10. These results show that one can obtain differential activity of the ED with only one hindering entity, when that one hindering entity is a surface. Enhanced hindrance would be obtained with a second hindering entity.
11. In the next study, a genetic construct was prepared where the steric hindrance to formation of an active β-galactosidase enzyme by complexing with the EA came from a cellular membrane and a protein at the other terminus. By employing a construct that expresses a protein that is directed to the cell membrane, where the protease cleavage site and ED are extracellular and having a protein as the extracellular terminus, the formation of β-galactosidase is substantially suppressed. The strategy for preparation of the DNA construct having the formula GST-ED-Factor Xa Cleavage Site-β2 Adrenergic Receptor (β2AR) is as follows:

12. Plasmid pGST-PL-FX-b2AR was constructed in two steps. First, a DNA segment encoding GST and flanked by AgeI restriction sites was amplified by PCR using pGEX-6P-1 (Amersham) as template DNA. The PCR primers

Figure 10:
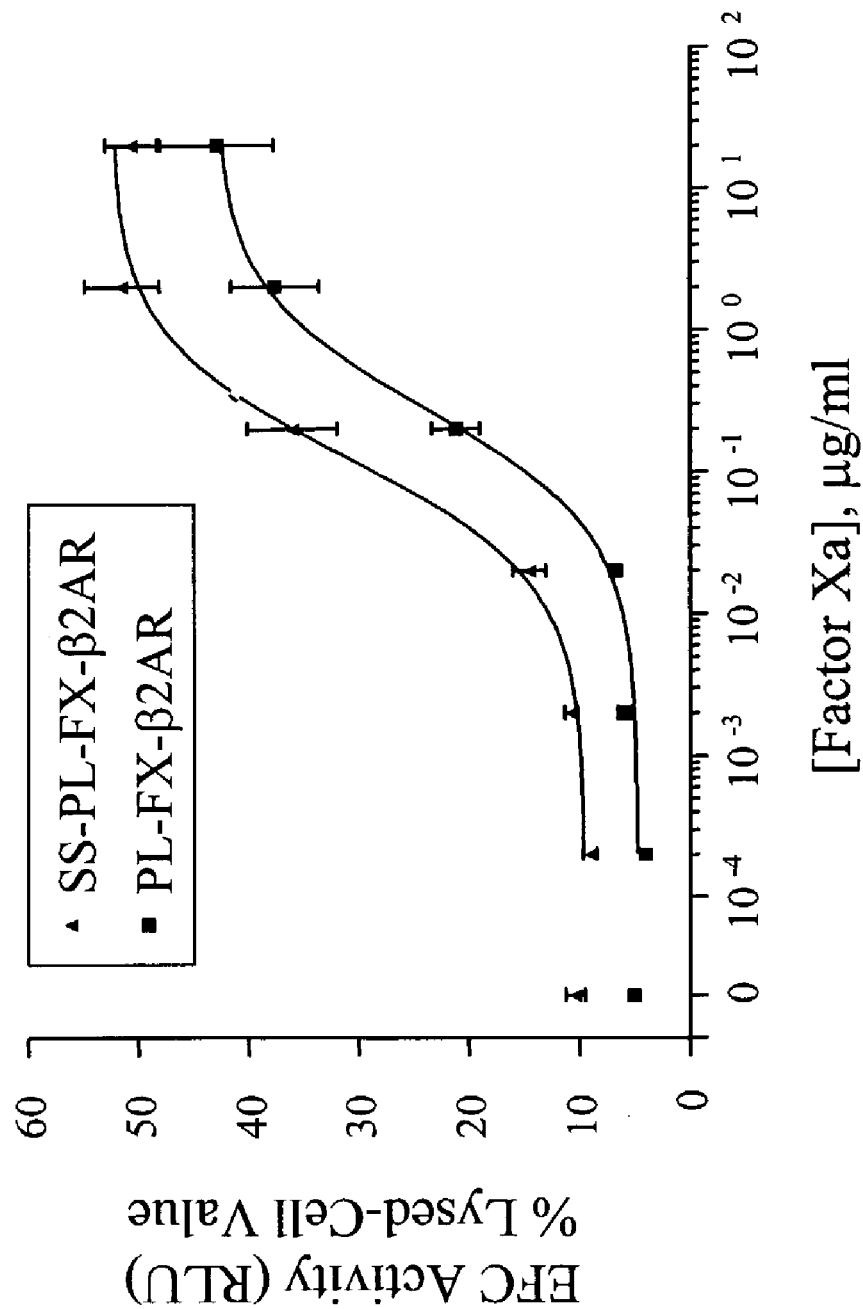
FIG. 10 is a plot of the effect of adding a signal sequence to a genetic construct on the available surface concentration of the expression product of the genetic construct.

```
GST Forward (5'-AAAACCGGTATGTCCCCTATACTAGGTTA-3')   (SEQ ID NO: 16)
and
GST Reverse (5'-AAAACCGGTTTATCCGATTTTGGAGGATGGT-3') (SEQ ID NO: 7)
``` both introduce an AgeI restriction site (underlined). In the second step, the PCR-amplified DNA was digested with AgeI and ligated to pPL-FX-b2AR DNA that had been prepared by digestion with AgeI followed by treatment with alkaline phosphatase. The unique AgeI site in pPL-FX-b2AR is immediately 5' to the sequences encoding ProLabel (PL). The final construct, pGST-PL-FX-b2AR, was confirmed by restriction analysis and DNA sequencing. The complete plasmid sequence (SEQ ID:NO 6) is as shown in FIG. 8.
13. Using the above construct, the construct is transfected into HEK293 cells. The resulting transfectants are selected for expression as described above. Assays are performed with and without FXa and the construct is shown to be substantially inhibited from forming β-galactosidase when the ED is part of the fusion protein and bound to the cell membrane and is active when released from the fusion protein upon cleavage with FXa. The results are further substantiated by the above and following observations.
14. That FXa does not cause cell lysis was established by using cells transfected with an IκB-ED construct, where only background activity was observed over a concentration range of FXa of about $10^{-4}$ to $2 \times 10^1$ µg/mL. See FIG. 9.
15. It was found that, adding the cleavable hemagglutinin signal sequence (MKTTIALSYIFCLVFA) (SEQ ID NO: 18), N-terminal to ED further enhanced the transport of the fusion protein to the surface to increase its concentration at the surface. This resulted in a significant increase in signal. See FIG. 10. The signal sequence (SS) expressing DNA construct, pSS-PL-FX-b2AR, was made by replacing the AgeII XhoI PL fragment of pPL-FX-b2AR with a AgeII XhoI fragment encoding the cleavable signal sequence followed by PL. The SS-PL fragment was obtained by PCR amplification of PL encoding DNA using pPL-FX-b2AR as a template and PCR primers that introduced an AgeI site and SS sequences 5' of the PL sequences.
16. The above result demonstrates that a single protein bound to the ED through a protease cleavage site is insufficient for providing a significant difference in enzyme activity. As observed, the construct is as active as the cleaved ED, indicating that the β2-AR has substantially no effect on the activity of the ED in forming active β-galactosidase.

17. In the final study, the effect of an FXa inhibitor was evaluated. The assay was as follows: HEK293 transient transfectant cells expressing Signal Sequence-PL-FXa-b2AR were seeded into individual wells of a 96-well plate at a density that gave ~80% confluency following 2 days growth. Two sets of assay buffers were prepared in PBSC/BSA, one without and one with FXa at 4 µg/mL. Each set represented a 5-fold serial dilution series of the protease inhibitor cocktail Complete Mini, EDTA-free (Roche Cat. No. 1 873 580), with the highest system concentration being 1× according to the manufacturer's instructions. The assay solutions were held at room temperature for 30 minutes after preparation to provide time for inhibition to occur. Culture fluid above the cells was removed by aspiration and replaced by 50 µL of the assay solutions described above, and the plate was incubated at room temperature for 1 hour. Eighty microliters of EA Core Buffer/EA Reagent (3:1) was added to each well and the plate was maintained at 37° C. for 1 hour. Finally 30 µL of CL substrate was added per well and the plate was incubated at room temperature protected from light. Readings were taken periodically on the Northstar plate reader from 15 minutes to 1 hour following substrate addition. It was shown that over the range of inhibitor concentration of 1× to ¹⁄₂₅× the RLUs varied from about 8,000 to about 11,000, demonstrating that the subject methodology can be used for screening the effect of protease inhibitors in a rapid and convenient assay. The background was shown to be substantially constant in the absence of FXa.

18. It is evident from the above results that a novel sensitive specific assay is provided for determining enzyme activity by employing a protein reagent having two sterically hindering proteins joined by a linker comprising a protease susceptible linkage and an enzyme donor fragment. The sterically hindering proteins serve to substantially reduce background, so that an accurate amplified signal may be obtained for each cleavage event. Since the enzyme activity may cleave a plurality of protein reagents and each cleavage is further amplified by the reporter enzyme, one obtains a robust signal even in the presence of small amounts of the target enzyme. The protein reagent is readily synthesized using recombinant techniques. Small assay volumes and automated procedures can be employed.

19. Although the invention has been described with reference to the above examples, it will be understood that modifications and variations are encompassed within the spirit and scope of the invention. Accordingly, the invention is limited only by the following claims.

What is claimed is:

1. A method for determining target protease activity in a sample, employing a protein reagent comprising first and second hindering entities, the hindering entities linked together by an enzyme donor ("ED") fragment and an amino acid sequence comprising a covalent bond susceptible to cleavage by said target protease activity, wherein said ED in the absence of at least one hindering entity is able to form an active indicator enzyme with an enzyme acceptor ("EA") fragment, wherein cleavage of the cleavable sequence by the target protease produces a protein reagent fragment active with said EA to produce an active indicator enzyme, wherein indicator enzyme activity is related to said target protease activity, and wherein said protein reagent fragment is at least 5 times as active as said protein reagent in complexing with said EA in forming active indicator enzyme, said method comprising:
combining said protein reagent, said sample, enzyme acceptor and indicator enzyme substrate for a time sufficient for said target protease activity to cleave said covalent bond; and
measuring the indicator enzyme activity as an indication of the protease activity.

2. A method according to claim 1, wherein said enzyme donor fragment and said enzyme acceptor fragment consist substantially of fragments of said enzyme and said fragments of said enzyme independently complex to form an active indicator enzyme.

3. A method according to claim 1, wherein said enzyme donor fragment is a first fragment of said indicator enzyme fused to a first binding protein to form a first fusion protein and said enzyme acceptor fragment is a second fragment of said indicator enzyme fused to a second binding protein to form a second fusion protein, wherein said first and second fragments of said indicator enzyme do not independently complex to form an active enzyme and upon complex formation of said first and second binding proteins an active indicator enzyme is formed.

4. A method according to claim 1, wherein each of said first and second hindering entities are proteins of at least about 5 kDa.

5. A method according to claim 1, wherein said protein reagent fragment is at least about 10 times as active as said protein reagent in complexing with said enzyme acceptor in forming active indicator enzyme.

6. A method according to claim 1, wherein said enzyme donor is of from about 37 to 120 amino acids.

7. A method according to claim 1, wherein said covalent bond is within 50 amino acids of said enzyme donor.

8. A method according to claim 1, wherein one of said hindering entities is a surface or a liposome.

9. A method for determining protease activity in a sample, employing a protein reagent comprising first and second hindering entities, the hindering entities linked together by an enzyme donor ("ED") fragment of β-galactosidase and an amino acid sequence comprising a covalent bond specifically susceptible to cleavage by said protease activity, wherein said ED in the absence of at least one hindering entity is able to form with an enzyme acceptor fragment of β-galactosidase to form an active β-galactosidase, wherein cleavage of the cleavable amino acid seciuence by said target protease produces a protein reagent fragment active with said enzyme acceptor to produce an active β-galactosidase, wherein β-galactosidase activity is related to said protease activity, and wherein said protein reagent fragment is at least 5 times as active as said protein reagent in complexing with said EA in forming active β-galactosidase, said method comprising:
combining said protein reagent, said sample, enzyme acceptor and β-gaiactosidase substrate for a time sufficient for said enzyme activity to cleave said amino acid sequence; and
measuring the β-galactosidase activity as an indication of the enzyme activity.

10. A method according to claim 9, wherein at least one of said first and second hindering entities is a protein of at least 10 kDa.

11. A method according to claim 9, wherein said amino acid sequence is within 50 amino acids of said enzyme donor.

12. A method according to claim 9, wherein said protease is a serine/threonine hydrolase.

13. A method according to claim 9, wherein said protease is a metalloproteinase.

14. A method according to claim 9, wherein said hindering entities are proteins.

15. A method according to claim 14, wherein said first protein is glutathione-S-transferase.

16. A method according to claim 9, wherein at least one of said first and second hindering entities is linked through a non-covalent linkage.

17. A method for determining target protease activity in a sample, employing a protein reagent comprising first and second hindering entities, the hindering entities linked together by an enzyme donor ("ED") fragment of β-galactosidase and an amino acid sequence comprising a covalent bond susceptible to cleavage by said target protease activity, said protein reagent substantially inactive in complexing with an enzyme acceptor fragment of β-galactosidase to form an active β-galactosidase, wherein cleavage of the cleavable amino acid seciuence by said target protease produces a protein reagent fragment comprising said ED in the absence of at least one hindering entity to form an active β-galactosidase with an enzyme acceptor fragment and said protein reagent fragment is of at least about 125 kDa active with said enzyme acceptor, wherein indicator enzyme activity is related to said target protease activity, and wherein said hindering entities result in at least a 5-fold reduction in β-galactosidase activity in said sample, said method comprising:
combining said protein reagent, said sample, enzyme acceptor and β-galactosidase substrate for a time sufficient for said target protease activity to cleave said covalent bond; and
measuring the indicator enzyme activity as an indication of the protease activity.

18. A method according to claim 17, wherein one of said hindering entities is a surface or liposome to which said protein reagent is bound.

19. A method according to claim 17, wherein at least one of said hindering entities is a protein of at least about 20 kDa.

20. A method according to claim 17, wherein said protease is a caspase.

* * * * *

UNITED STATES PATENT AND TRADEMARK OFFICE
CERTIFICATE OF CORRECTION

PATENT NO. : 7,256,011 B2 Page 1 of 1
APPLICATION NO. : 10/353908
DATED : August 14, 2007
INVENTOR(S) : Pyare Khanna et al.

It is certified that error appears in the above-identified patent and that said Letters Patent is hereby corrected as shown below:

COLUMN 37

Line 61, delete "seciuence" after the word "acid" and insert --sequence--.

COLUMN 38

Line 7, delete "gaiactosidase" after "Beta-" and insert --galactosidase--.

Line 38, delete "seciuence" after the word "acid" and insert --sequence--.

Signed and Sealed this

Fourth Day of December, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 4010
<212> TYPE: DNA
<213> ORGANISM: Artificial Sequence
<220> FEATURE:
<223> OTHER INFORMATION: Description of Artificial Sequence: Synthetic
      PQE30-ED-IL4 sequence

<400> SEQUENCE: 1

```
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc agctccaatt cactggccgt cgttttacaa     180
cgtcgtgact gggaaaaccc tggcgttacc caacttaatc gccttgcagc acatccccct     240
ttcgccagct ggcgtaatag cgaagaggcc cgcaccgatc gcccttccca acagttgcgc     300
agcctgaatg gcgaagcatg cgagctcggt accagatctg tcgaccacaa gtgcgatatc     360
accttacagg agatcatcaa aactttgaac agcctcacag agcagaagac tctgtgcacc     420
gagttgaccg taacagacat ctttgctgcc tccaagaaca caactgagaa ggaaaccttc     480
tgcagggctg cgactgtgct ccggcagttc tacagccacc atgagaagga cactcgctgc     540
ctgggtgcga ctgcacagca gttccacagg cacaagcagc tgatccgatt cctgaaacgg     600
ctcgacagga acctctgggg cctggcgggc ttgaattcct gtcctgtgaa ggaagccaac     660
cagagtacgt tggaaaactt cttggaaagg ctaaagacga tcatgagaga gaaatattca     720
aagtgttcga gctgaaagct taattagctg agcttggact cctgttgata gatccagtaa     780
tgacctcaga actccatctg gatttgttca gaacgctcgg ttgccgccgg gcgttttttta     840
```

| | | | |
|---|---|---|---|
| ttggtgagaa | tccaagctag | cttggcgaga | ttttcaggag ctaaggaagc taaaatggag | 900 |
| aaaaaaatca | ctggatatac | caccgttgat | atatcccaat ggcatcgtaa agaacatttt | 960 |
| gaggcatttc | agtcagttgc | tcaatgtacc | tataaccaga ccgttcagct ggatattacg | 1020 |
| gcctttttaa | agaccgtaaa | gaaaaataag | cacaagtttt atccggcctt tattcacatt | 1080 |
| cttgcccgcc | tgatgaatgc | tcatccgaaa | tttcgtatgg caatgaaaga cggtgagctg | 1140 |
| gtgatatggg | atagtgttca | cccttgttac | accgttttcc atgagcaaac tgaaacgttt | 1200 |
| tcatcgctct | ggagtgaata | ccacgacgat | ttccggcagt ttctacacat atattcgcaa | 1260 |
| gatgtggcgt | gttacggtga | aaacctggcc | tatttcccta aagggtttat tgagaatatg | 1320 |
| tttttcgtct | cagccaatcc | ctgggtgagt | tcaccagtt ttgatttaaa cgtggccaat | 1380 |
| atggacaact | tcttcgcccc | cgttttcacc | atgggcaaat attatacgca aggcgacaag | 1440 |
| gtgctgatgc | cgctggcgat | tcaggttcat | catgccgttt gtgatggctt ccatgtcggc | 1500 |
| agaatgctta | atgaattaca | acagtactgc | gatgagtggc agggcggggc gtaattttt | 1560 |
| taaggcagtt | attggtgccc | ttaaacgcct | ggggtaatga ctctctagct tgaggcatca | 1620 |
| aataaaacga | aaggctcagt | cgaaagactg | gcctttcgt tttatctgtt gtttgtcggt | 1680 |
| gaacgctctc | ctgagtagga | caaatccgcc | ctctagagct gcctcgcgcg tttcggtgat | 1740 |
| gacggtgaaa | acctctgaca | catgcagctc | ccggagacgg tcacagcttg tctgtaagcg | 1800 |
| gatgccggga | gcagacaagc | ccgtcagggc | gcgtcagcgg gtgttggcgg gtgtcggggc | 1860 |
| gcagccatga | cccagtcacg | tagcgatagc | ggagtgtata ctggcttaac tatgcggcat | 1920 |
| cagagcagat | tgtactgaga | gtgcaccata | tgcggtgtga ataccgcac agatgcgtaa | 1980 |
| ggagaaaata | ccgcatcagg | cgctcttccg | cttcctcgct cactgactcg ctgcgctcgg | 2040 |
| tcgttcggct | gcggcgagcg | gtatcagctc | actcaaaggc ggtaatacgg ttatccacag | 2100 |
| aatcagggga | taacgcagga | aagaacatgt | gagcaaaagg ccagcaaaag gccaggaacc | 2160 |
| gtaaaaaggc | cgcgttgctg | gcgtttttcc | ataggctccg cccccctgac gagcatcaca | 2220 |
| aaaatcgacg | ctcaagtcag | aggtggcgaa | acccgacagg actataaaga taccaggcgt | 2280 |
| ttccccctgg | aagctccctc | gtgcgctctc | ctgttccgac cctgccgctt accggatacc | 2340 |
| tgtccgcctt | tctcccttcg | ggaagcgtgg | cgctttctca tagctcacgc tgtaggtatc | 2400 |
| tcagttcggt | gtaggtcgtt | cgctccaagc | tgggctgtgt gcacgaaccc cccgttcagc | 2460 |
| ccgaccgctg | cgccttatcc | ggtaactatc | gtcttgagtc aacccggta agacacgact | 2520 |
| tatcgccact | ggcagcagcc | actggtaaca | ggattagcag agcgaggtat gtaggcggtg | 2580 |
| ctacagagtt | cttgaagtgg | tggcctaact | acggctacac tagaaggaca gtatttggta | 2640 |
| tctgcgctct | gctgaagcca | gttaccttcg | gaaaaagagt tggtagctct tgatccggca | 2700 |
| aacaaaccac | cgctggtagc | ggtggttttt | ttgtttgcaa gcagcagatt acgcgcagaa | 2760 |
| aaaaaggatc | tcaagaagat | cctttgatct | tttctacggg gtctgacgct cagtggaacg | 2820 |
| aaaactcacg | ttaagggatt | ttggtcatga | gattatcaaa aaggatcttc acctagatcc | 2880 |
| ttttaaatta | aaaatgaagt | tttaaatcaa | tctaaagtat atatgagtaa acttggtctg | 2940 |
| acagttacca | atgcttaatc | agtgaggcac | ctatctcagc gatctgtcta tttcgttcat | 3000 |
| ccatagttgc | ctgactcccc | gtcgtgtaga | taactacgat acgggagggc ttaccatctg | 3060 |
| gccccagtgc | tgcaatgata | ccgcgagacc | cacgctcacc ggctccagat ttatcagcaa | 3120 |
| taaaccagcc | agccggaagg | gccgagcgca | gaagtggtcc tgcaacttta tccgcctcca | 3180 |
| tccagtctat | taattgttgc | cgggaagcta | gagtaagtag ttcgccagtt aatagtttgc | 3240 |

```
gcaacgttgt tgccattgct acaggcatcg tggtgtcacg ctcgtcgttt ggtatggctt    3300
cattcagctc cggttcccaa cgatcaaggc gagttacatg atcccccatg ttgtgcaaaa    3360
aagcggttag ctccttcggt cctccgatcg ttgtcagaag taagttggcc gcagtgttat    3420
cactcatggt tatggcagca ctgcataatt ctcttactgt catgccatcc gtaagatgct    3480
tttctgtgac tggtgagtac tcaaccaagt cattctgaga atagtgtatg cggcgaccga    3540
gttgctcttg cccggcgtca atacgggata ataccgcgcc acatagcaga actttaaaag    3600
tgctcatcat tggaaaacgt tcttcggggc gaaaactctc aaggatctta ccgctgttga    3660
gatccagttc gatgtaaccc actcgtgcac ccaactgatc ttcagcatct tttactttca    3720
ccagcgtttc tgggtgagca aaaacaggaa ggcaaaatgc cgcaaaaaag ggaataaggg    3780
cgacacggaa atgttgaata ctcatactct tcctttttca atattattga agcatttatc    3840
agggttattg tctcatgagc ggatacatat ttgaatgtat ttagaaaaat aaacaaatag    3900
gggttccgcg cacatttccc cgaaaagtgc cacctgacgt ctaagaaacc attattatca    3960
tgacattaac ctataaaaat aggcgtatca cgaggccctt tcgtcttcac               4010

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 2
cacggatcca gctccaattc actggccgtc g                                   31

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 3
cgcggatcca agctttcagc tcgaacactt tgaata                              36

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      Bam HI ED-IL4 fragment ligated into pGEX 6p-1

<400> SEQUENCE: 4

Leu Glu Val Leu Phe Gln Gly Pro Leu Gly Ser Pro Glu Phe Pro Gly
 1               5                  10                  15

Arg Leu Glu Arg Pro His
            20

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence: Synthetic
      Bam HI ED-IL4 fragment ligated into pGEX 6p-1
<220> FEATURE:
<221> NAME/KEY: CDS
<222> LOCATION: (1)..(66)
```

-continued

<400> SEQUENCE: 5

```
ctg gaa gtt ctg ttc cag ggg ccc ctg gga tcc ccg gaa ttc ccg ggt    48
Leu Glu Val Leu Phe Gln Gly Pro Leu Gly Ser Pro Glu Phe Pro Gly
 1               5                  10                  15 cga ctc gag cgg ccg cat                                             66
Arg Leu Glu Arg Pro His
             20
```

<210> SEQ ID NO 6
<211> LENGTH: 6062
<212> TYPE: DNA
<213> ORGANISM: Artificial Sequence
<220> FEATURE:
<223> OTHER INFORMATION: Description of Artificial Sequence: Synthetic pGST-PL-FX-b2AR plasmid sequence

<400> SEQUENCE: 6

| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cgtcagatcc gctagcgcta | 600 |
| ccggtatgtc ccctatacta ggttattgga aaattaaggg ccttgtgcaa cccactcgac | 660 |
| ttcttttgga atatcttgaa gaaaaatatg aagagcattt gtatgagcgc gatgaaggtg | 720 |
| ataaatggcg aaacaaaaag tttgaattgg gtttggagtt tcccaatctt ccttattata | 780 |
| ttgatggtga tgttaaatta acacagtcta tggccatcat acgttatata gctgacaagc | 840 |
| acaacatgtt gggtggttgt ccaaaagagc gtgcagagat ttcaatgctt gaaggagcgg | 900 |
| ttttggatat tagatacggt gtttcgagaa ttgcatatag taaagacttt gaaactctca | 960 |
| aagttgattt tcttagcaag ctacctgaaa tgctgaaaat gttcgaagat cgtttatgtc | 1020 |
| ataaaacata tttaaatggt gatcatgtaa cccatcctga cttcatgttg tatgacgctc | 1080 |
| ttgatgttgt tttatacatg gacccaatgt gcctggatgc gttcccaaaa ttagtttgtt | 1140 |
| ttaaaaaacg tattgaagct atcccacaaa ttgataagta cttgaaatcc agcaagtata | 1200 |
| tagcatggcc tttgcagggc tggcaagcca gtttggtgg tggcgaccat cctccaaaat | 1260 |
| cggataaacc ggtcgccacc atgagctcca attcactggc cgtcgtttta caacgtcgtg | 1320 |
| actgggaaaa ccctggcgtt acccaactta tcgccttgc agcacatccc cctttcgcca | 1380 |
| gctggcgtaa tagcgaagag gcccgcaccg atcgccttc caacagttg cgcagcctga | 1440 |
| atggcgaacc ggactcagat ctcgagatcg aaggtcgtat ggggcaaccc gggaacggca | 1500 |
| gcgccttctt gctggcaccc aatagaagcc atgcgccgga ccacgacgtc acgcagcaaa | 1560 |
| gggacgaggt gtgggtggtg ggcatgggca tcgtcatgtc tctcatcgtc ctggccatcg | 1620 |
| tgtttggcaa tgtgctggtc atcacagcca ttgccaagtt cgagcgtctg cagacggtca | 1680 |
| ccaactactt catcacttca ctggcctgtg ctgatctggt catgggcctg gcagtggtgc | 1740 |

```
cctttggggc cgcccatatt cttatgaaaa tgtggacttt tggcaacttc tggtgcgagt    1800
tttggacttc cattgatgtg ctgtgcgtca cggccagcat tgagaccctg tgcgtgatcg    1860
cagtggatcg ctactttgcc attacttcac ctttcaagta ccagagcctg ctgaccaaga    1920
ataaggcccg ggtgatcatt ctgatggtgt ggattgtgtc aggccttacc tccttcttgc    1980
ccattcagat gcactggtac cgggccaccc accaggaagc catcaactgc tatgccaatg    2040
agacctgctg tgacttcttc acgaaccaag cctatgccat tgcctcttcc atcgtgtcct    2100
tctacgttcc cctggtgatc atggtcttcg tctactccag ggtctttcag gaggccaaaa    2160
ggcagctcca gaagattgac aaatctgagg ccgcttcca tgtccagaac cttagccagg    2220
tggagcagga tgggcggacg gggcatggac tccgcagatc ttccaagttc tgcttgaagg    2280
agcacaaagc cctcaagacg ttaggcatca tcatgggcac tttcacccTc tgctggctgc    2340
ccttcttcat cgttaacatt gtgcatgtga tccaggataa cctcatccgt aaggaagttt    2400
acatcctcct aaattggata ggctatgtca attctggttt caatcccctt atctactgcc    2460
ggagcccaga tttcaggatt gccttccagg agcttctgtg cctgcgcagg tcttcttTga    2520
aggcctatgg gaatggctac tccagcaacg gcaacacagg ggagcagagt ggatatcacg    2580 tgaacagga aagaaaat aaactgctgt gtgaagacct cccaggcacg gaagactttg    2640
tgggccatca aggtactgtg cctagcgata acattgattc acaagggagg aattgtagta    2700
caaatgactc actgctgtaa ggatccaccg gatctagata actgatcata atcagccata    2760
ccacatttgt agaggtttta cttgctttaa aaaacctccc acacctcccc ctgaacctga    2820
aacataaaat gaatgcaatt gttgttgtta acttgtttat tgcagcttat aatggttaca    2880
aataaagcaa tagcatcaca aatttcacaa ataaagcatt ttttcactg cattctagtt    2940 gtggtttgtc caaactcatc aatgtatctt aacgcgtaaa ttgtaagcgt taatatttg    3000 ttaaaattcg cgttaaattt ttgttaaatc agctcatttt ttaaccaata ggccgaaatc    3060
ggcaaaatcc cttataaatc aaaagaatag accgagatag ggttgagtgt tgttccagtt    3120
tggaacaaga gtccactatt aaagaacgtg gactccaacg tcaaagggcg aaaaaccgtc    3180
tatcagggcg atggcccact acgtgaacca tcaccctaat caagttttTt ggggtcgagg    3240
tgccgtaaag cactaaatcg gaaccctaaa gggagcccCC gatttagagc ttgacgggga    3300
aagccggcga acgtggcgag aaaggaaggg aagaaagcga aggagcgggc gctagggcg    3360 ctggcaagtg tagcggtcac gctgcgcgta accaccacac ccgccgcgct taatgcgccg    3420
ctacagggcg cgtcaggtgg cacttttcgg ggaaatgtgc gcggaacccc tatttgttta    3480
tttttctaaa tacattcaaa tatgtatccg ctcatgagac aataaccctg ataaatgctt    3540
caataatatt gaaaaaggaa gagtcctgag gcggaaagaa ccagctgtgg aatgtgtgtc    3600
agttagggtg tggaaagtcc ccaggctccc cagcaggcag aagtatgcaa agcatgcatc    3660
tcaattagtc agcaaccagg tgtggaaagt ccccaggctc cccagcaggc agaagtatgc    3720
aaagcatgca tctcaattag tcagcaacca tagtcccgcc cctaactccg cccatcccgc    3780
ccctaactcc gcccagttcc gcccattctc cgccccatgg ctgactaatt ttttttattt    3840
atgcagaggc cgaggccgcc tcggcctctg agctattcca gaagtagtga ggaggctttt    3900
ttggaggcct aggcttttgc aaagatcgat caagagacag gatgaggatc gtttcgcatg    3960
attgaacaag atggattgca cgcaggttct ccggccgctt gggtggagag gctattcggc    4020
tatgactggg cacaacagac aatcggctgc tctgatgccg ccgtgttccg gctgtcagcg    4080
```

```
cagggcgcc cggttctttt tgtcaagacc gacctgtccg gtgccctgaa tgaactgcaa    4140
gacgaggcag cgcggctatc gtggctggcc acgacgggcg ttccttgcgc agctgtgctc    4200
gacgttgtca ctgaagcggg aagggactgg ctgctattgg gcgaagtgcc ggggcaggat    4260
ctcctgtcat ctcaccttgc tcctgccgag aaagtatcca tcatggctga tgcaatgcgg    4320
cggctgcata cgcttgatcc ggctacctgc ccattcgacc accaagcgaa acatcgcatc    4380
gagcgagcac gtactcggat ggaagccggt cttgtcgatc aggatgatct ggacgaagag    4440
catcaggggc tcgcgccagc cgaactgttc gccaggctca aggcgagcat gcccgacggc    4500
gaggatctcg tcgtgaccca tggcgatgcc tgcttgccga atatcatggt ggaaaatggc    4560
cgcttttctg gattcatcga ctgtggccgg ctgggtgtgg cggaccgcta tcaggacata    4620
gcgttggcta cccgtgatat tgctgaagag cttggcggcg aatgggctga ccgcttcctc    4680
gtgctttacg gtatcgccgc tcccgattcg cagcgcatcg ccttctatcg ccttcttgac    4740
gagttcttct gagcgggact ctggggttcg aaatgaccga ccaagcgacg cccaacctgc    4800
catcacgaga tttcgattcc accgccgcct tctatgaaag gttgggcttc ggaatcgttt    4860
tccgggacgc cggctggatg atcctccagc gcggggatct catgctggag ttcttcgccc    4920
accctagggg gaggctaact gaaacacgga aggagacaat accggaagga cccgcgcta    4980 tgacggcaat aaaagacag aataaaacgc acggtgttgg gtcgtttgtt cataaacgcg    5040
gggttcggtc ccagggctgg cactctgtcg ataccccacc gagacccat tggggccaat    5100 acgcccgcgt tcttcctttt tccccacccc accccccaag ttcgggtgaa ggcccagggc    5160
tcgcagccaa cgtcggggcg gcaggccctg ccatagcctc aggttactca tatatacttt    5220
agattgattt aaaacttcat ttttaattta aaaggatcta ggtgaagatc cttttgata    5280 atctcatgac caaaatccct aacgtgagt tttcgttcca ctgagcgtca gaccccgtag    5340
aaaagatcaa aggatcttct tgagatcctt tttttctgcg cgtaatctgc tgcttgcaaa    5400
caaaaaaacc accgctacca gcggtggttt gtttgccgga tcaagagcta ccaactcttt    5460
ttccgaaggt aactggcttc agcagagcgc agataccaaa tactgtcctt ctagtgtagc    5520
cgtagttagg ccaccacttc aagaactctg tagcaccgcc tacatacctc gctctgctaa    5580
tcctgttacc agtggctgct gccagtggcg ataagtcgtg tcttaccggg ttggactcaa    5640
gacgatagtt accggataag gcgcagcggt cgggctgaac ggggggttcg tgcacacagc    5700
ccagcttgga gcgaacgacc tacaccgaac tgagatacct acagcgtgag ctatgagaaa    5760
gcgccacgct tcccgaaggg agaaaggcgg acaggtatcc ggtaagcggc agggtcggaa    5820
caggagagcg cacagggag cttccagggg gaaacgcctg gtatctttat agtcctgtcg    5880
ggtttcgcca cctctgactt gagcgtcgat ttttgtgatg ctcgtcaggg gggcggagcc    5940
tatggaaaaa cgccagcaac gcggcctttt tacggttcct ggccttttgc tggccttttg    6000
ctcacatgtt ctttcctgcg ttatcccctg attctgtgga taaccgtatt accgccatgc    6060
at                                                                  6062
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 7

Asp Glu Val Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 8

Asp Asp Val Asp
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 9

Trp Glu His Asp
1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 10

Lys Lys Arg Lys Arg Arg
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 11

Gly Ser Gly Ile Phe Leu Glu Thr Ser Leu
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 12

Val Pro Arg Gly Ser
1               5

<210> SEQ ID NO 13
<211> LENGTH: 4
<212> TYPE: PRT
<213> ORGANISM: Artificial Sequence
<220> FEATURE:

```
<223> OTHER INFORMATION: Description of Artificial Sequence:
      Illustrative recognition peptide

<400> SEQUENCE: 13

Ile Glu Gly Arg
 1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:
      Illustrative recognition peptide

<400> SEQUENCE: 14

Asp Asp Asp Asp Lys
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:
      Illustrative recognition peptide
<220> FEATURE:
<221> NAME/KEY: MOD_RES
<222> LOCATION: (6)
<223> OTHER INFORMATION: Gln or Gly

<400> SEQUENCE: 15

Leu Glu Val Leu Phe Xaa Pro
 1               5

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 16
aaaaccggta tgtcccctat actaggtta                                    29

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 17
aaaaccggtt tatccgattt tggaggatgg t                                 31

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      signal sequence

<400> SEQUENCE: 18

Met Lys Thr Ile Ile Ala Leu Ser Tyr Ile Phe Cys Leu Val Phe Ala
 1               5                  10                  15
```